(12) United States Patent
Watanabe et al.

(10) Patent No.: US 7,261,995 B2
(45) Date of Patent: Aug. 28, 2007

(54) NITROGEN-CONTAINING ORGANIC COMPOUND, CHEMICALLY AMPLIFIED RESIST COMPOSITION AND PATTERNING PROCESS

(75) Inventors: Takeru Watanabe, Joetsu (JP); Koji Hasegawa, Joetsu (JP); Katsuya Takemura, Joetsu (JP); Kazumi Noda, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 271 days.

(21) Appl. No.: 11/110,927

(22) Filed: Apr. 21, 2005

(65) Prior Publication Data

US 2005/0238993 A1    Oct. 27, 2005

(30) Foreign Application Priority Data

Apr. 23, 2004  (JP)  ............................. 2004-128478

(51) Int. Cl.
*G03C 1/73*   (2006.01)
(52) U.S. Cl. .................... 430/270.1; 549/432; 549/436
(58) Field of Classification Search ............ 430/270.1; 549/432, 436
See application file for complete search history.

(56) References Cited

U.S. PATENT DOCUMENTS

| | | | |
|---|---|---|---|
| 4,491,628 A | 1/1985 | Ito et al. | |
| 5,310,619 A | 5/1994 | Crivello et al. | |
| 5,580,695 A | 12/1996 | Murata et al. | |
| 5,658,706 A | 8/1997 | Niki et al. | |
| 5,744,281 A | 4/1998 | Niki et al. | |
| 6,004,724 A | 12/1999 | Yamato et al. | |
| 6,261,738 B1 | 7/2001 | Asakura et al. | |
| 6,746,818 B2 * | 6/2004 | Kinsho et al. | ............ 430/270.1 |

FOREIGN PATENT DOCUMENTS

| | | |
|---|---|---|
| JP | 63-27829 A | 2/1988 |
| JP | 2-27660 B2 | 6/1990 |
| JP | 5-232706 A | 9/1993 |
| JP | 7-134419 A | 5/1995 |
| JP | 9-95479 A | 4/1997 |
| JP | 9-208554 A | 8/1997 |
| JP | 9-230588 A | 9/1997 |
| JP | 9-301948 A | 11/1997 |
| JP | 2906999 B2 | 4/1999 |
| JP | 2000-314956 A | 11/2000 |

OTHER PUBLICATIONS

W. Hinsberg et al., Journal of Photopolymer Science and Technology, "Fundamental Studies of Airborne Chemical Contamination of Chemically Amplified Resists", vol. 6, No. 4, pp. 535-546 (1993).
Teruhiko Kumada et al., Journal of Photopolymer Science and Technology, "Study On Over-Top Coating of Positive Chemical Amplification Resists For KrF Excimer Laser Lithography", vol. 6, No. 4, pp. 571-574 (1993).
Jun Hatakeyama et al., Journal of Photopolymer Science and Technology, "Investigation of Discrimination Enhancement with New Modeling for Poly-Hydroxystyrene Positive Resists", vol. 13, No. 4, pp. 519-524 (2000).
Koji Arimitsu et al., Journal of Photopolymer Science and Technology, "Sensitivity Enhancement of Chemical-Amplification-Type Photoimaging Materials by Acetoacetic Acid Derivatives", vol. 8, No. 1, pp. 43-46 (1995).
Koji Arimitsu et al., Journal of Photopolymer Science and Technology, "Effect of Phenolic Hydroxyl Residues On The Improvement of Acid-Proliferation-Type Photoimaging Materials", vol. 9, No. 1, pp. 29-30 (1996).

* cited by examiner

*Primary Examiner*—Barbara Gilliam
*Assistant Examiner*—Ponder Thompson-Rummel
(74) *Attorney, Agent, or Firm*—Birch, Stewart, Kolasch & Birch, LLP

(57) ABSTRACT

Chemically amplified resist compositions comprising nitrogen-containing organic compounds having a 7-oxanorbornane-2-carboxylic ester structure have resolution and provide a precise pattern profile and are useful in microfabrication using electron beams or deep-UV light.

4 Claims, No Drawings

NITROGEN-CONTAINING ORGANIC COMPOUND, CHEMICALLY AMPLIFIED RESIST COMPOSITION AND PATTERNING PROCESS

CROSS-REFERENCE TO RELATED APPLICATION

This non-provisional application claims priority under 35 U.S.C. §119(a) on Patent Application No. 2004-128478 filed in Japan on Apr. 23, 2004, the entire contents of which are hereby incorporated by reference.

TECHNICAL FIELD

The present invention relates to a novel nitrogen-containing organic compound, a chemically amplified resist composition comprising the same and suitable for microfabrication technology, and a patterning process using the resist composition.

BACKGROUND ART

Of the efforts currently being made to achieve a finer pattern rule in the drive for higher integration and operating speeds in LSI devices, deep-ultraviolet lithography is thought to hold particular promise as the next generation in microfabrication technology. Deep-UV lithography is capable of fabrication to dimensions of 0.2 µm or less and, when a resist having low light absorption is used, can form patterns with sidewalls that are nearly perpendicular to the substrate. One technology that has attracted a good deal of attention recently utilizes high-intensity KrF and ArF excimer lasers as the deep-UV light source. This technology is being used in mass-scale production, prompting a desire for resists having a low light absorption and a high sensitivity.

Acid-catalyzed, positive-working chemically amplified resists (e.g., U.S. Pat. No. 4,491,628 and U.S. Pat. No. 5,310,619, or JP-B 2-27660 and JP-A 63-27829) developed in response to the above needs are endowed with excellent properties, including a high sensitivity, high resolution and good dry-etching resistance, which make them especially promising as resists for deep-UV lithography.

However, one problem with chemically amplified resists is that, when the standing time from exposure to post exposure bake (PEB) is long, the line pattern formed during patterning acquires a "T-top" profile characterized by widening at the top of the pattern. This defect is called "post exposure delay" (PED). Another problem with such resists is "footing," which is a widening of the resist pattern close to the substrate that occurs on a basic substrate, particularly a silicon nitride or titanium nitride substrate. The T-top effect is believed to result from a decrease in solubility at the surface of the resist film, and the footing effect at the substrate surface appears to arise from a decline in solubility near the substrate. An additional problem is that acid-labile group elimination is a dark reaction which proceeds during the interval between the exposure step and the PEB step, reducing the final dimensions of the pattern lines. These problems represent major drawbacks to the practical use of chemically amplified resists. Because of such defects, prior-art positive-working chemically amplified resists are difficult to control dimensions in the lithographic process. Dimensional control is also lost during dry etching of the substrate. See, for example, W. Hinsberg et al., Journal of Photopolymer Science and Technology, Vol. 6, No. 4, 535-546 (1993); and T. Kumada et al., ibid., 571-574.

In positive-working chemically amplified resists, the problems of PED and footing on the substrate surface are believed to be caused in large part by basic compounds which are either airborne or present on the surface of the substrate. The acid at the surface of the resist film that has been generated by exposure reacts with airborne bases and is deactivated. Prolonged standing until post-exposure bake results in a corresponding increase in the amount of deactivated acid, making it more difficult for the acid-labile groups to decompose. A substantially insolubilized layer thus forms at the surface, giving the resist pattern a T-top profile.

It is well-known in the art that the addition of a nitrogen-containing compound can check the influence of airborne bases, and is thus effective also against PED (see, for example, JP-A 5-232706 and JP-A 7-134419). Familiar nitrogen-containing compounds having significant addition effects include amine compounds and amide compounds. Specific examples include pyridine, polyvinylpyridine, aniline, N-methylaniline, N,N-dimethylaniline, o-toluidine, m-toluidine, p-toluidine, 2,4-lutidine, quinoline, isoquinoline, formamide, N-methylformamide, N,N-dimethylformamide, acetamide, N-methylacetamide, N,N-dimethylacetamide, 2-pyrrolidone, N-methylpyrrolidone, imidazole, α-picoline, β-picoline, γ-picoline, o-aminobenzoic acid, m-aminobenzoic acid, p-aminobenzoic acid, 1,2-phenylenediamine, 1,3-phenylenediamine, 1,4-phenylenediamine, 2-quinolinecarboxylic acid, 2-amino-4-nitrophenol, and 2-(p-chlorophenyl)-4,6-trichloromethyl-s-triazine.

These nitrogen-containing compounds are weak bases and can alleviate the T-top problem, but such compounds are unable to control the reaction when highly reactive acid-labile groups are used; that is, they cannot control acid diffusion fully. With the addition of a weak base, the dark reactions in PED in particular proceed in unexposed areas, causing slimming of the line dimensions and a loss of film thickness from the line surface (called top-loss) during PED. To overcome such problems, it is desirable to add a strong base. However, a higher basicity is not necessarily better. For example, good effects cannot be obtained with the addition of the following super-strong bases:

DBU (1,8-diazabicyclo[5.4.0]-7-undecene),

DBN (1,5-diazabicyclo[4.3.0]-5-nonene) and proton sponge (1,8-bis(dimethylamino)naphthalene) or quaternary ammonium hydroxides such as tetramethylammonium hydroxide.

The addition of a nitrogen-containing compound having an excellent ability to capture the generated acids kinetically works well to increase the contrast and thereby achieve a high resolution. The dissociation constants of the acid and base within water can be explained in terms of pKa, but the kinetic acid capturing ability within the resist film is not directly related to the pKa of the nitrogen-containing compound. This is discussed by Hatakeyama et al. in Journal of Photopolymer Science and Technology, Vol. 13, No. 4, pp. 519-524 (2000). It is also known that the profile of a pattern are dictated by the identity of a nitrogen-containing organic compound used.

SUMMARY OF THE INVENTION

It is therefore an object of the invention to provide a chemically amplified resist composition which exhibits a high resolution and forms a precisely configured pattern, when processed by photolithography for micropatterning, especially lithography using a light source such as a KrF laser, ArF laser, $F_2$ laser, extremely short UV, electron beam or x-ray. Another object of the invention is to provide a patterning process which uses the resist composition. A further object of the invention is to provide a novel nitrogen-containing organic compound suited for use in the resist composition.

In a first aspect, the invention provides a nitrogen-containing organic compound having a 7-oxanorbornane-2-carboxylic ester structure, represented by the general formula (1).

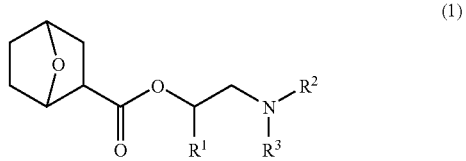

(1)

Herein $R^1$ is hydrogen or a straight, branched or cyclic $C_1$-$C_{10}$ alkyl group; $R^2$ and $R^3$ are each independently a $C_1$-$C_{20}$ alkyl group, $C_6$-$C_{20}$ aryl group or $C_7$-$C_{20}$ aralkyl group which may contain at least one polar functional group such as ether, carbonyl, ester, alcohol, sulfide, nitrile, amine, imine or amide, and in which some hydrogen atoms may be substituted with halogen atoms, or $R^2$ and $R^3$, taken together, may form a heterocyclic or heteroaromatic ring of 2 to 20 carbon atoms with the nitrogen atom to which they are attached.

The nitrogen-containing organic compound having a 7-oxanorbornane-2-carboxylic ester structure represented by formula (1) can be readily prepared in high yields by the method to be described below, and when added in a proper amount, enables to formulate a resist composition which exhibits a high resolution and forms a precisely configured pattern. For a certain application, a proper choice of R1, R2 and R3 enables to optimize resist characteristics including a pattern profile.

In a second aspect, the present invention provides a chemically amplified resist composition comprising at least one nitrogen-containing organic compound having a 7-oxanorbornane-2-carboxylic ester structure represented by formula (1). The composition exhibits a high resolution and forms a precisely configured pattern.

In a third aspect, the present invention provides a chemically amplified resist composition comprising (A) the nitrogen-containing organic compound having a 7-oxanorbornane-2-carboxylic ester structure represented by formula (1), (B) an organic solvent, (C) a base resin having an acid labile group-protected acidic functional group which is alkali-insoluble or substantially alkali-insoluble, but becomes alkali-soluble when the acid labile group is eliminated, and (D) a photoacid generator. The composition exhibits a high resolution and forms a precisely configured pattern.

Still further, the present invention provides a patterning process comprising the steps of (1) applying the chemically amplified resist composition defined above onto a substrate; (2) heat treating the applied resist, then exposing the heat-treated resist through a photomask to high-energy radiation having a wavelength of up to 300 nm or an electron beam; and (3) heat treating the exposed resist, then developing the resist with a liquid developer. The patterning process is successful in forming a resist pattern having a high resolution and satisfactory profile.

The chemically amplified resist compositions prepared by compounding the nitrogen-containing organic compounds having a specific structure exhibit a high resolution, form patterns of good profile, and are useful in lithographic micropatterning using electron beams and deep UV. The nitrogen-containing organic compounds exert best effects when compounded in resists adapted for KrF laser, ArF laser, $F_2$ laser, EUV, EB or x-ray lithography, making the resists ideal as a micropatterning material in VLSI fabrication. The compositions are applicable not only to ordinary photolithography, but also to immersion lithography.

DESCRIPTION OF THE PREFERRED EMBODIMENTS

As used herein, the term "carboxylic ester" refers to carboxylic acid ester. Abbreviation Me stands for methyl, Et for ethyl, and Ac for acetyl.

Nitrogen Compound

The inventors sought for a compound which when compounded in chemically amplified resist compositions, is effective for achieving a high resolution and defining a satisfactory pattern profile. The inventors have discovered that a nitrogen-containing organic compound having a 7-oxanorbornane-2-carboxylic ester structure, represented by formula (1), can be combined in proper amounts with a base resin and other components to formulate a chemically amplified photoresist composition which exhibits a high resolution and forms a precisely configured pattern. When heat treatment prior to exposure, i.e., prebaking is effected at a higher temperature, typically at or above 120° C., conventional resist compositions tend to form defectively configured patterns due to increased top-loss, but the resist compositions of the invention overcome such problems and achieve significant improvements.

The nitrogen-containing compounds to be compounded in chemically amplified resist compositions are nitrogen-containing organic compounds having a 7-oxanorbornane-2-carboxylic ester structure, represented by the general formula (1).

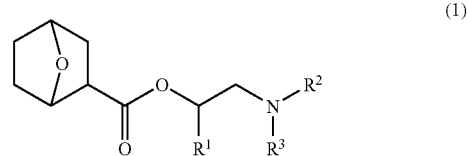

(1)

In formula (1), $R^1$ is hydrogen or a straight, branched or cyclic $C_1$-$C_{10}$ alkyl group. Illustrative, non-limiting examples of suitable alkyl groups include methyl, ethyl, propyl, isopropyl, butyl, isobutyl, s-butyl, t-butyl, pentyl, cyclopentyl, hexyl, cyclohexyl, octyl, and decyl.

$R^2$ and $R^3$ are independently selected from among alkyl groups of 1 to 20 carbon atoms, preferably 1 to 10 carbon atoms, aryl groups of 6 to 20 carbon atoms, preferably 6 to 10 carbon atoms, and aralkyl groups of 7 to 20 carbon atoms, preferably 7 to 11 carbon atoms, which may contain at least one polar functional group such as ether (—O—), carbonyl (—CO—), ester (—COO—), alcohol (—OH), sulfide (—S—), nitrile (—C≡N), amine, imine or amide, and in which some hydrogen atoms may be substituted with halogen atoms. Alternatively, $R^2$ and $R^3$, taken together, may form a heterocyclic or heteroaromatic ring of 2 to 20 carbon atoms with the nitrogen atom to which they are attached.

Note that amine, imine and amide are represented by

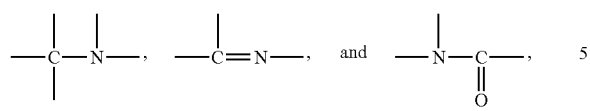

respectively.

Illustrative examples of $C_1$-$C_{20}$ alkyl groups which may contain one or more polar functional groups such as ether, carbonyl, ester, alcohol, sulfide, nitrile, amine, imine or amide include, but are not limited to, methyl, ethyl, propyl, isopropyl, butyl, isobutyl, 2-butyl, t-butyl, pentyl, cyclopentyl, hexyl, cyclohexyl, octyl, decyl, hexadecyl, eicosyl, 2-hydroxyethyl, 2-hydroxypropyl, 3-hydroxybutyl, 2-hydroxybutyl, 2,3-dihydroxypropyl, 2-methoxyethyl, 2-ethoxyethyl, 2-(methoxymethoxy)ethyl, 2-(2-methoxyethoxy)ethyl, 4-methoxybutyl, tetrahydrofurfuryl, 2-oxopropyl, 4-oxocyclohexyl, 2-acetoxyethyl, 10-acetoxydecyl, 2,3-diacetoxypropyl, methoxycarbonylmethyl, 2-methoxycarbonylethyl, 2-ethoxycarbonylethyl, 3-ethoxycarbonylpropyl, 2-(methylthio)ethyl, cyanomethyl, 2-cyanoethyl, 3-cyanopropyl, 2-dimethylaminoethyl, acetyl, and 2-carbamoylethyl. Illustrative examples of $C_6$-$C_{20}$ aryl groups which may contain one or more polar functional groups such as ether, carbonyl, ester, alcohol, sulfide, nitrile, amine, imine or amide include, but are not limited to, phenyl, naphthyl, anthryl, phenanthryl, pyrenyl, naphthacenyl, fluorenyl, toluyl, xylyl, biphenyl, decylphenyl, methoxyphenyl, hydroxyphenyl, acetylphenyl, methoxycarbonylphenyl, acetoxyphenyl, methylthiophenyl, cyanophenyl, dimethoxyphenyl, diacetoxyphenyl, and dihydroxyphenyl. Illustrative examples of $C_7$-$C_{20}$ aralkyl groups which may contain one or more polar functional groups such as ether, carbonyl, ester, alcohol, sulfide, nitrile, amine, imine or amide include, but are not limited to, benzyl, 1-phenylethyl, 2-phenylethyl, 14-phenyltetradecyl, naphthylmethyl, anthrylmethyl, phenanthrylmethyl, pyrenylmethyl, naphthacenylmethyl, fluorenylmethyl, toluylmethyl, xylylmethyl, decylphenylmethyl, methoxyphenylmethyl, hydroxyphenylmethyl, acetylphenylmethyl, methoxycarbonylphenylmethyl, acetoxyphenylmethyl, methylthiophenylmethyl, cyanophenylmethyl, dimethoxyphenylmethyl, diacetoxyphenylmethyl, and dihydroxyphenylmethyl. When $R^2$ and $R^3$ bond together to form a heterocyclic or heteroaromatic ring of 2 to 20 carbon atoms with the nitrogen atom to which they are attached, examples of the heterocyclic or heteroaromatic ring include aziridine, azetidine, pyrrolidine, piperidine, piperadine, morpholine, thiomorpholine, 4-hydroxypiperidine, aza-12-crown-4, aza-15-crown-5, pyrrolidinone, piperidinone, ϵ-caprolactam, dihydroxyindole, pyrrole, pyrazole, imidazole, triazole, tetrazole, indole, benzpyrazole, benzimidazole, phenoxazine, carbazole, purine and substituted forms of the foregoing.

Illustrative, non-limiting examples of the nitrogen-containing organic compounds represented by formula (1) are given below.

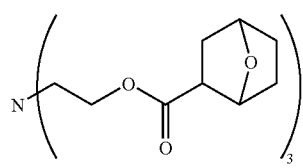

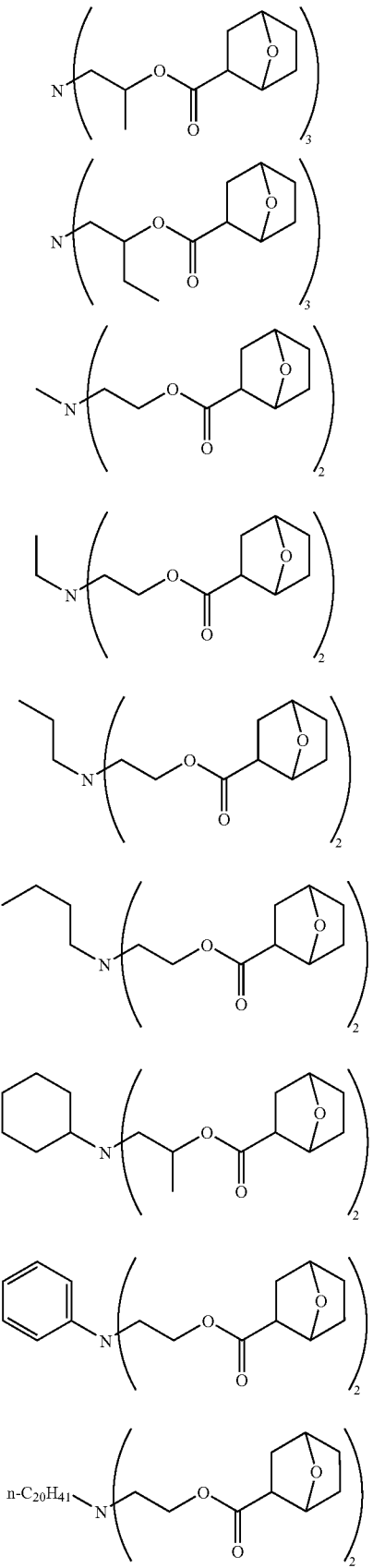

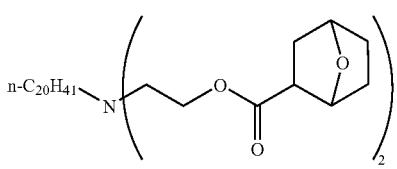

-continued
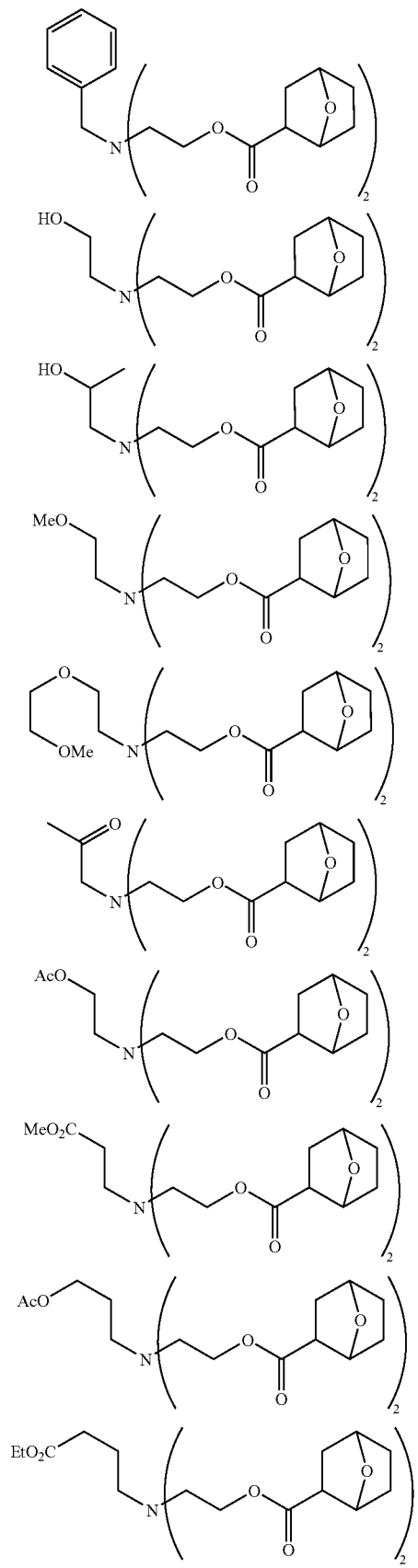
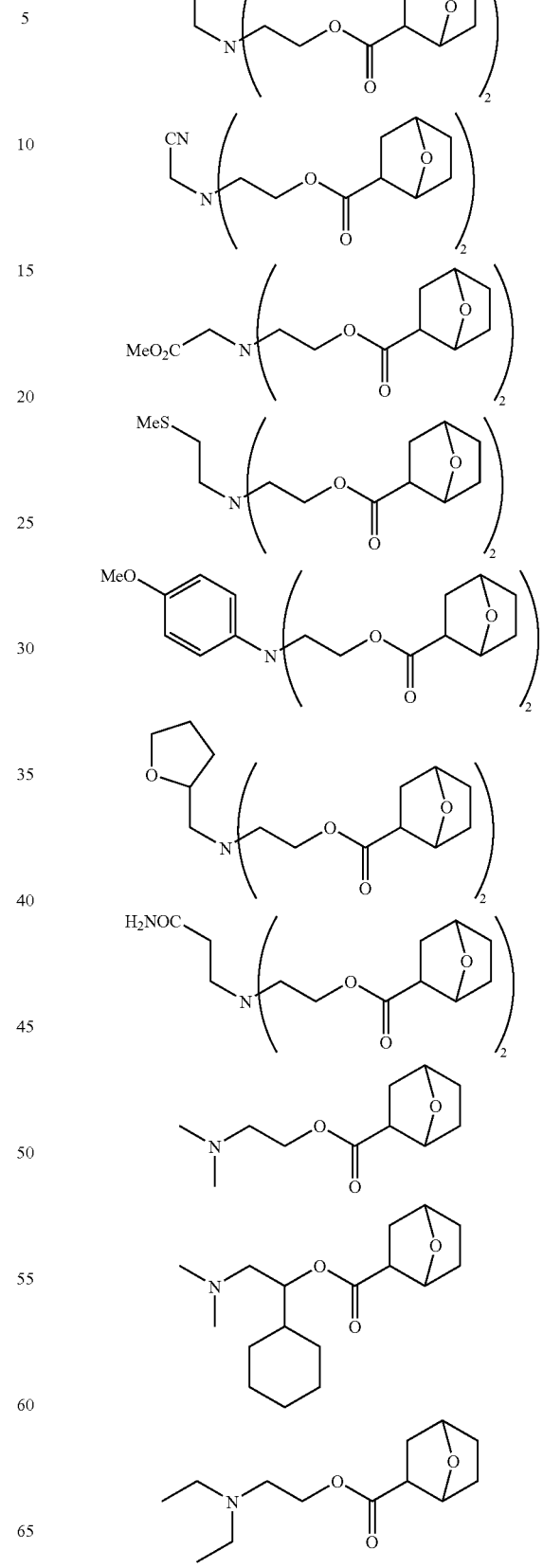

-continued
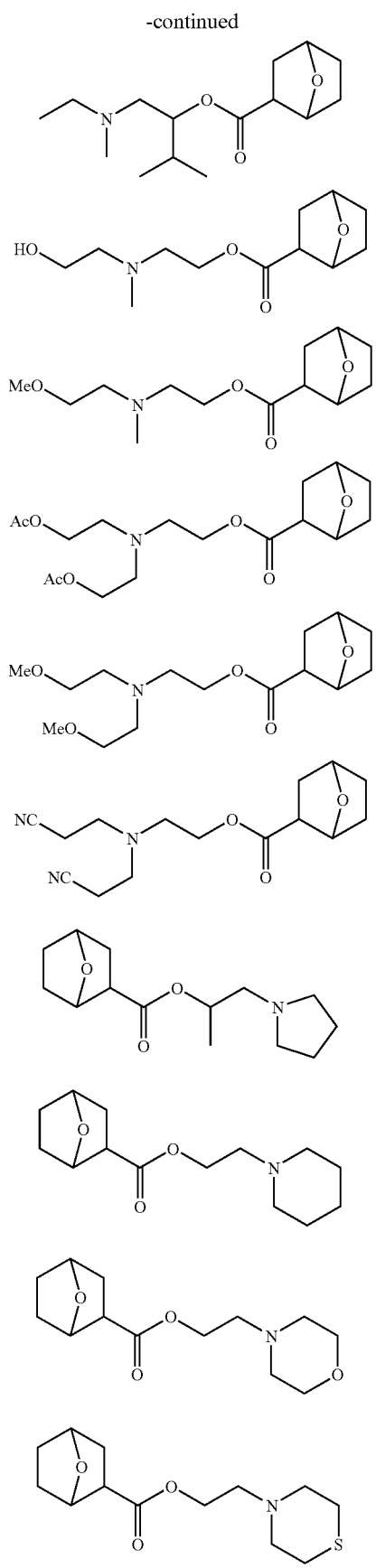
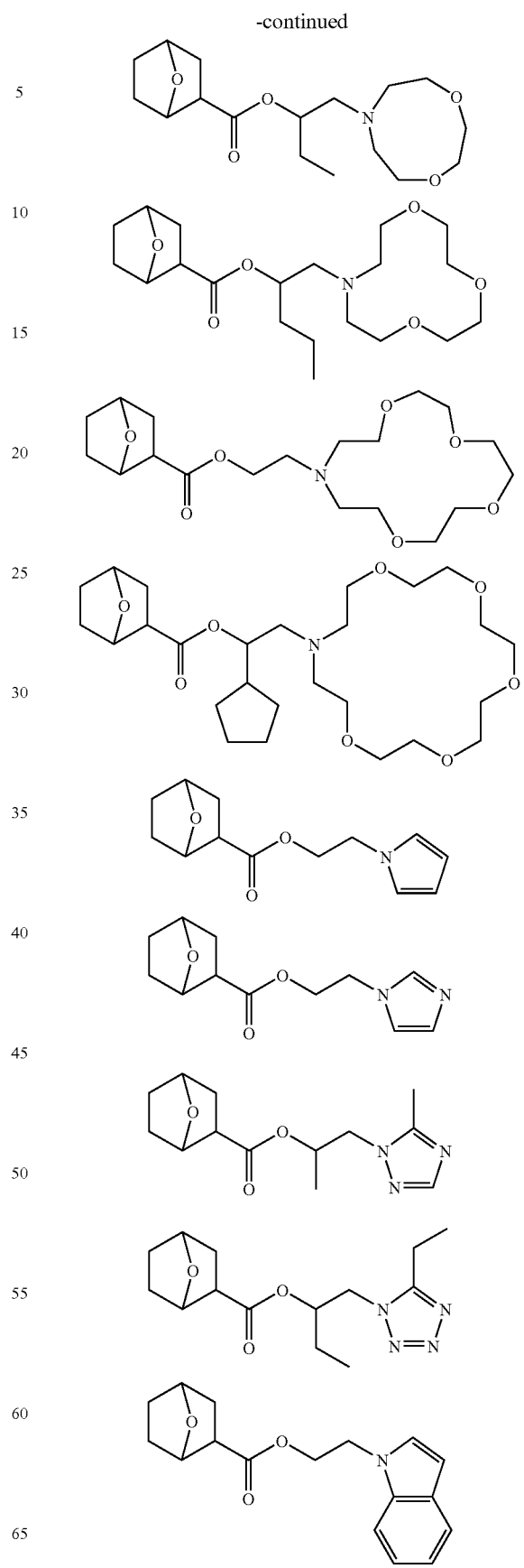

-continued

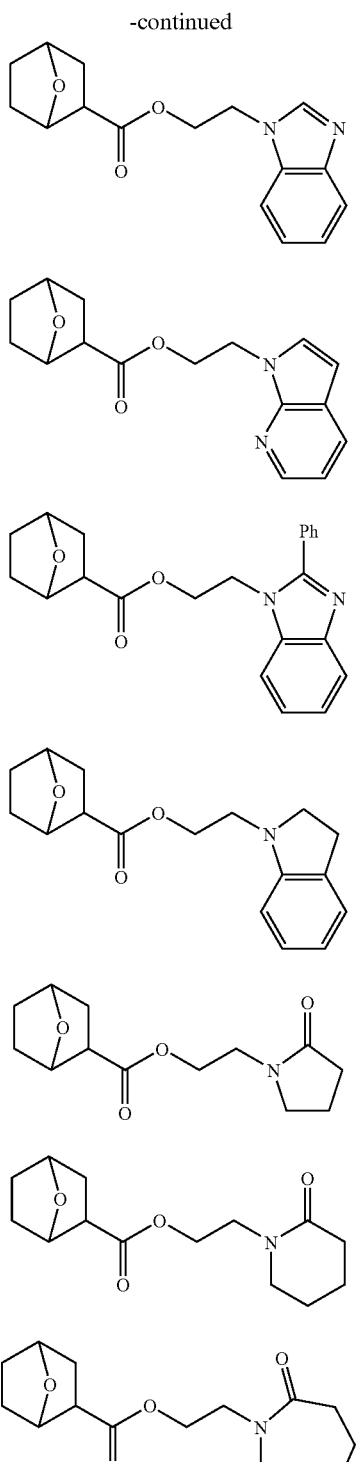

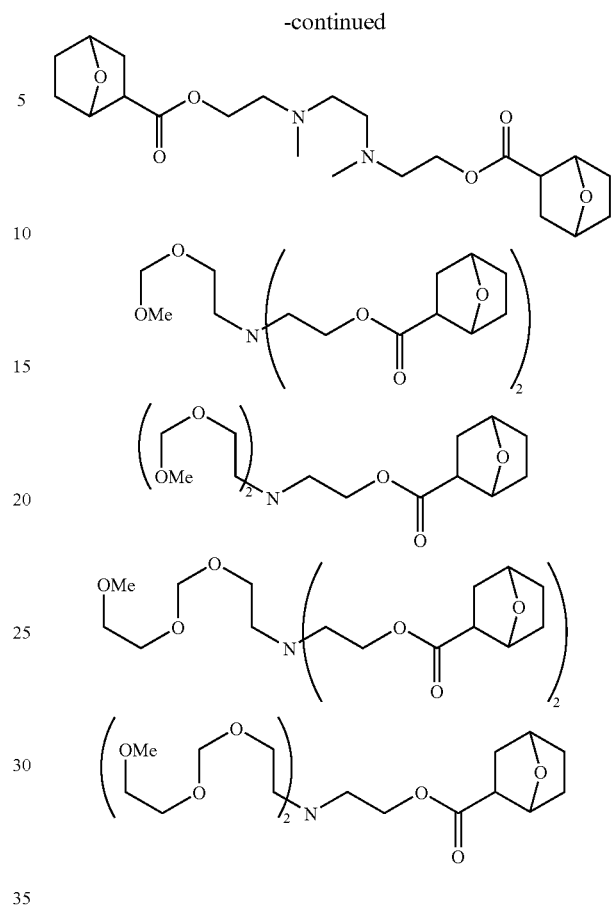

In these nitrogen-containing organic compounds having a 7-oxanorbornane-2-carboxylic ester structure within the molecule, the 7-oxanorbornane-2-carboxylic ester group has a high affinity to acids. It is anticipated that the presence of that group at an appropriate position in proximity to the nitrogen atom enables to rapidly capture the acid generated from the photoacid generator, and the 7-oxanorbornane-2-carboxylic ester structure itself affects the distribution of the nitrogen-containing organic compound in the resist film. As a result, the photoresist composition having added thereto the nitrogen-containing organic compound is endowed with an ability to achieve a high resolution and a excellent pattern profile. By selecting for a certain application an optimal structure from among many possible nitrogen-containing organic compounds having a 7-oxanorbornane-2-carboxylic ester structure according to the invention, the volatility, basicity, and acid-capturing rate of the nitrogen-containing organic compound and the acid diffusion rate within the resist can be suitably adjusted to a particular combination of the resist polymer with the photoacid generator. This eventually enables to adjust resist material characteristics such as pattern profile.

The nitrogen-containing organic compounds of formula (1) are novel. They are prepared by an optimum method that is selected in accordance with the structure of the compound. A two-step method involving synthesis of an alcohol compound through addition reaction of a compound having —NH group to an epoxide equivalent and subsequent esterification of the alcohol compound is typical although the method is not limited thereto. This typical method is described below in detail.

In the first step, an alcohol compound (4) is synthesized through addition reaction of a compound having —NH group (3) to an epoxide equivalent (2), as shown by the following scheme.

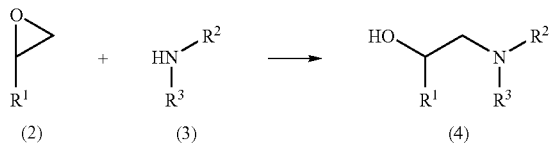

Herein $R^1$, $R^2$ and $R^3$ are as defined above.

Like conventional processes involving addition reaction of amine compounds to epoxides, the reaction may be conducted in a solvent and in the presence of an acid or base catalyst, if desired. The epoxide equivalent is typically an epoxide compound as shown by formula (2) while α-halohydrin compounds and cyclic carbonate compounds may be used in some cases.

The second step is esterification of the alcohol compound as shown by the following scheme.

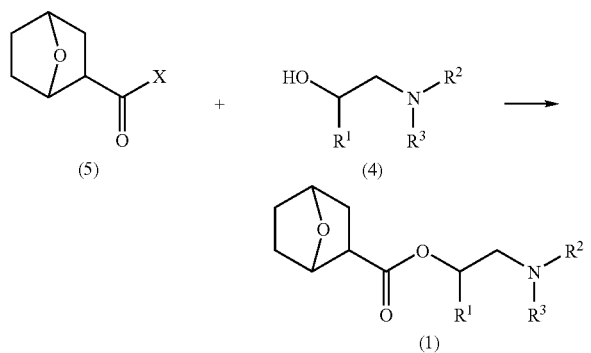

Herein $R^1$, $R^2$ and $R^3$ are as defined above, and X is a leaving group such as a halogen atom, acyloxy group, alkylsulfonyloxy or aryloxy group, or a hydroxyl group or an alkoxy group.

Where X in formula (5) is a leaving group such as a halogen atom, acyloxy group, alkylsulfonyloxy or aryloxy group, the relevant reaction is acylation of alcohol using an acylating agent, which reaction may be conducted in accordance with a customary procedure as used for acylation in the presence of base catalysts. Where X in formula (5) is —OH, the relevant reaction is esterification between alcohol and carboxylic acid, which reaction may be conducted in accordance with a customary procedure as used for esterification in the presence of acid catalysts. Where X in formula (5) is —OR wherein R is alkyl, the relevant reaction is transesterification between alcohol and carboxylic ester, which reaction may be conducted in accordance with a customary procedure as used for transesterification in the presence of base catalyst or Lewis acid catalysts. Following the reaction, the target compound, i.e., nitrogen-containing organic compound is isolated from the reaction mixture by a conventional aqueous work-up. If necessary, the target compound can be purified by an ordinary method such as distillation, chromatography or recrystallization. Alternatively, instead of the aqueous work-up, the reaction mixture may be directly subjected to purification.

Resist Composition

As previously described, the nitrogen-containing organic compound of the invention is effective as a basic compound component to be formulated in a chemically amplified resist composition. The chemically amplified resist composition of the invention is typically defined as comprising (A) a nitrogen-containing organic compound of formula (1), (B) an organic solvent, (C) a base resin having an acid labile group-protected acidic functional group which is alkali-insoluble or substantially alkali-insoluble, but becomes alkali-soluble when the acid labile group is eliminated, and (D) a photoacid generator.

In the inventive resist composition, an appropriate amount of the nitrogen-containing organic compound (A) compounded is 0.01 to 2 parts by weight, desirably 0.01 to 1 part by weight per 100 parts by weight of the base resin (C). Outside the range, less amounts of the nitrogen-containing compound may fail to achieve the desired effect whereas larger amounts may lower the sensitivity of the resist.

Organic Solvent B

The organic solvent used herein may be any organic solvent in which the nitrogen-containing organic compound, base resin, photoacid generator, and other components are soluble. Illustrative, non-limiting, examples of the organic solvent include ketones such as cyclohexanone and methyl n-amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone. These solvents may be used alone or in combinations of two or more thereof. Of the above organic solvents, it is recommended to use diethylene glycol dimethyl ether, 1-ethoxy-2-propanol, propylene glycol monomethyl ether acetate, and mixtures thereof because the photoacid generator is most soluble therein.

An appropriate amount of the organic solvent used is about 200 to 1,000 parts, especially about 400 to 800 parts by weight per 100 parts by weight of the base resin.

Base Polymer C

The base polymers used as component (C) in the inventive compositions include polyhydroxystyrene (PHS), and copolymers of hydroxystyrene with styrene, (meth)acrylic acid esters or other polymerizable olefinic compounds, for KrF excimer laser resist use; (meth)acrylic acid ester polymers, alternating copolymers of cycloolefin with maleic anhydride, copolymers further containing vinyl ethers or (meth)acrylic acid esters, polynorbornene, and ring-opening metathesis polymerized cycloolefins, for ArF excimer laser resist use; and fluorinated forms of the foregoing polymers (for both KrF and ArF laser uses) and polymers resulting from ring-closure polymerization using fluorinated dienes for $F_2$ excimer laser resist use. Silicon-substituted forms of the foregoing polymers and polysilsesquioxane polymers are useful for the bilayer resists. The base resin is not limited to the polymers of these systems. The base polymers may be used alone or in admixture of two or more. In the case of positive resist compositions, it is a common practice to substitute acid labile groups for hydroxyl groups on phenol, carboxyl groups or fluorinated alkyl alcohols for reducing the rate of dissolution in unexposed regions.

The acid labile groups to be introduced into the base polymers may be selected from a variety of such groups, preferably from acetal groups of 2 to 30 carbon atoms and tertiary alkyl groups of 4 to 30 carbon atoms having the formulae (C1) and (C2), respectively.

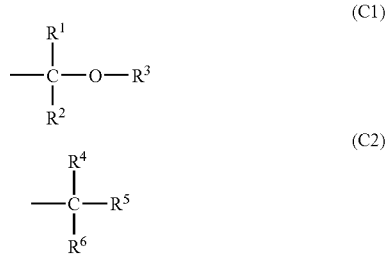

In formulae (C1) and (C2), $R^1$ and $R^2$ each are hydrogen or a straight, branched or cyclic alkyl group of 1 to 20 carbon atoms, preferably 1 to 12 carbon atoms, which may contain a heteroatom such as oxygen, sulfur, nitrogen or fluorine, $R^3$, $R^4$, $R^5$ and $R^6$ each are a straight, branched or cyclic alkyl group, aryl group or aralkyl group of 1 to 20 carbon atoms, preferably 1 to 12 carbon atoms, which may contain a heteroatom such as oxygen, sulfur, nitrogen or fluorine. A pair of $R^1$ and $R^2$, a pair of $R^1$ and $R^3$, a pair of $R^2$ and $R^3$, a pair of $R^4$ and $R^5$, a pair of $R^4$ and $R^6$, or a pair of $R^5$ and $R^6$, taken together, may form a ring of 3 to 20 carbon atoms, preferably 3 to 12 carbon atoms, with the carbon or oxygen atom to which they are attached.

Illustrative examples of the acetal group of formula (C1) include, but are not limited to, methoxymethyl, ethoxymethyl, propoxymethyl, butoxymethyl, isopropoxymethyl, t-butoxymethyl, 1-methoxyethyl, 1-methoxypropyl, 1-methoxybutyl, 1-ethoxyethyl, 1-ethoxypropyl, 1-ethoxybutyl, 1-propoxyethyl, 1-propoxypropyl, 1-propoxybutyl, 1-cyclopentyloxyethyl, 1-cyclohexyloxyethyl, 2-methoxyisopropyl, 2-ethoxyisopropyl, 1-phenoxyethyl, 1-benzyloxyethyl, 1-phenoxypropyl, 1-benzyloxypropyl, 1-adamantyloxyethyl, 1-adamantyloxypropyl, 2-tetrahydrofuryl, 2-tetrahydro-2H-pyranyl, 1-(2-cyclohexanecarbonyloxyethoxy) ethyl, 1-(2-cyclohexanecarbonyloxyethoxy)propyl, 1-[2-(1-adamantylcarbonyloxy)ethoxy]ethyl, and 1-[2-(1-adamantylcarbonyloxy)ethoxyl]propyl.

Illustrative examples of the tertiary alkyl group of formula (C2) include, but are not limited to, t-butyl, t-pentyl, 1-ethyl-1-methylpropyl, 1,1-diethylpropyl, 1,1,2-trimethylpropyl, 1-adamantyl-1-methylethyl, 1-methyl-1-(2-norbornyl)ethyl, 1-methyl-1-(tetrahydrofuran-2-yl)ethyl, 1-methyl-1-(7-oxanorbornan-2-yl)ethyl, 1-methylcyclopentyl, 1-ethylcyclopentyl, 1-propylcyclopentyl, 1-cyclopentylcyclopentyl, 1-cyclohexylcyclopentyl, 1-(2-tetrahydrofuryl)cyclopentyl, 1-(7-oxanorbornan-2-yl)cyclopentyl, 1-methylcyclohexyl, 1-ethylcyclohexyl, 1-cyclopentylcyclohexyl, 1-cyclohexylcyclohexyl, 2-methyl-2-norbornyl, 2-ethyl-2-norbornyl, 8-methyl-8-tricyclo[5.2.1.0$^{2,6}$]decyl, 8-ethyl-8-tricyclo [5.2.1. 0$^{2,6}$]decyl, 3-methyl-3-tetracyclo[4.4.0.1$^{2,5}$.1$^{7,10}$] dodecyl, 3-ethyl-3-tetracyclo[4.4.0.1$^{2,5}$.1$^{7,10}$]dodecyl, 2-methyl-2-adamantyl, 2-ethyl-2-adamantyl, 1-methyl-3-oxo-1-cyclohexyl, 1-methyl-1-(tetrahydrofuran-2-yl)ethyl, 5-hydroxy-2-methyl-2-adamantyl, and 5-hydroxy-2-ethyl-2-adamantyl.

In the base resin, some hydrogen atoms of hydroxyl groups may be substituted with acid labile groups of the following general formula (C3a) or (C3b) for crosslinkage between molecules or within a molecule.

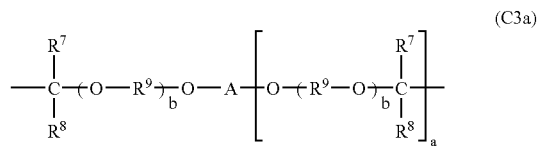

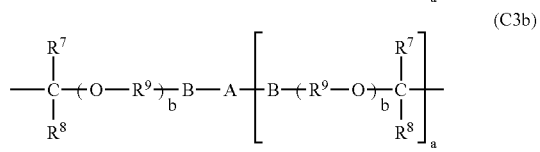

Herein, $R^7$ and $R^8$ each are hydrogen or a straight, branched or cyclic alkyl group of 1 to 8 carbon atoms, or $R^7$ and $R^8$, taken together, may form a ring, with the proviso that each of $R^7$ and $R^8$ is a straight or branched alkylene group of 1 to 8 carbon atoms when they form a ring. $R^9$ is a straight, branched or cyclic alkylene group of 1 to 10 carbon atoms. Letter "a" is an integer of 1 to 7, and "b" is 0 or an integer of 1 to 10. "A" is a (a+1)-valent aliphatic or alicyclic saturated hydrocarbon group, aromatic hydrocarbon group or heterocyclic group of 1 to 50 carbon atoms, which may have an intervening heteroatom and in which the hydrogen atom attached to a carbon atom may be partially replaced by a hydroxyl group, carboxyl group, carbonyl group or fluorine atom. B is —CO—O—, —NHCO—O— or —NHCONH—.

Illustrative examples of the crosslinking acetal linkages represented by formulae (C3a) and (C3b) are given below as (C3)-1 through (C3)-8, but not limited thereto.

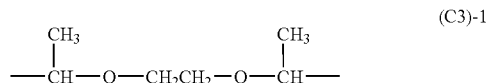
(C3)-1

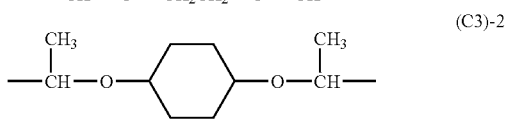
(C3)-2

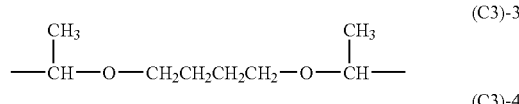
(C3)-3

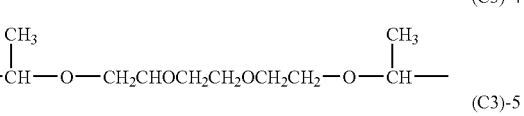
(C3)-4

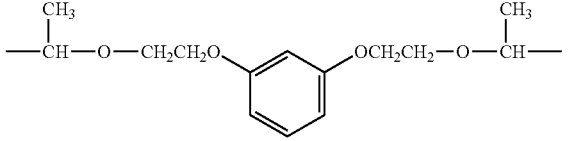
(C3)-5

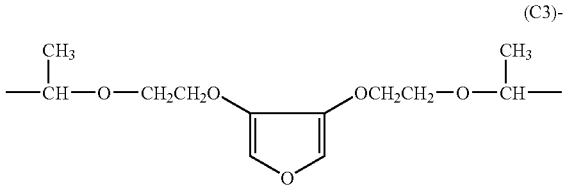
(C3)-6

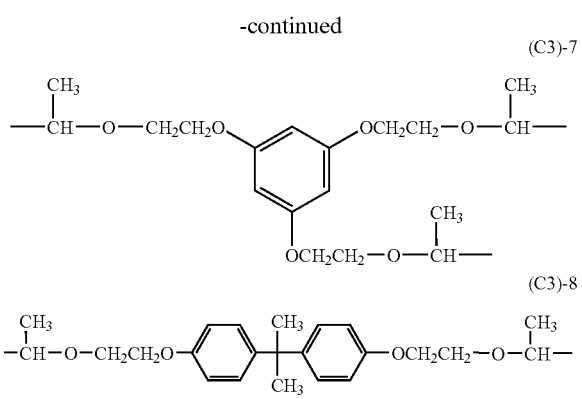

(C3)-7

(C3)-8

Preferably the base polymer has a weight average molecular weight (Mw) of 2,000 to 100,000. With Mw below 2,000, film formation and resolution may become poor. With Mw beyond 100,000, resolution may become poor or foreign matter may generate during pattern formation. Note that the Mw is determined by gel permeation chromatography (GPC) using polystyrene standards.

Photoacid Generator D

The resist composition further contains (D) a compound capable of generating an acid upon exposure to high-energy radiation, that is, a photoacid generator. Suitable photoacid generators include sulfonium salts, iodonium salts, sulfonyldiazomethane and N-sulfonyloxyimide photoacid generators. Exemplary photoacid generators are given below while they may be used alone or in admixture of two or more.

Sulfonium salts are salts of sulfonium cations with sulfonates. Exemplary sulfonium cations include triphenylsulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl) diphenylsulfonium, bis(3-tert-butoxyphenyl) phenylsulfonium, tris(3-tert-butoxyphenyl)sulfonium, (3,4-di-tert-butoxyphenyl)diphenylsulfonium, bis(3,4-di-tert-butoxyphenyl)phenylsulfonium, tris(3,4-di-tert-butoxyphenyl)sulfonium, diphenyl(4-thiophenoxyphenyl) sulfonium, (4-tert-butoxycarbonylmethyloxyphenyl) diphenylsulfonium, tris(4-tert-butoxycarbonylmethyloxyphenyl)sulfonium, (4-tert-butoxyphenyl)bis(4-dimethylaminophenyl)sulfonium, tris (4-dimethylaminophenyl)sulfonium, 2-naphthyldiphenylsulfonium, dimethyl-2-naphthylsulfonium, 4-hydroxyphenyldimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, and 2-oxo-2-phenylethylthiacyclopentanium. Exemplary sulfonates include trifluoromethanesulfonate, nonafluorobutanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, 4-(4'-toluenesulfonyloxy)benzenesulfonate, naphthalenesulfonate, camphorsulfonate, octanesulfonate, dodecylbenzenesulfonate, butanesulfonate, and methanesulfonate. Sulfonium salts based on combination of the foregoing examples are included.

Iodinium salts are salts of iodonium cations with sulfonates. Exemplary iodinium cations are aryliodonium cations including diphenyliodinium, bis(4-tert-butylphenyl)iodonium, 4-tert-butoxyphenylphenyliodonium, and 4-methoxyphenylphenyliodonium. Exemplary sulfonates include trifluoromethanesulfonate, nonafluorobutanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, 4-(4-toluenesulfonyloxy)benzenesulfonate, naphthalenesulfonate, camphorsulfonate, octanesulfonate, dodecylbenzenesulfonate, butanesulfonate, and methanesulfonate. Iodonium salts based on combination of the foregoing examples are included.

Exemplary sulfonyldiazomethane compounds include bissulfonyldiazomethane compounds and sulfonyl-carbonyldiazomethane compounds such as bis(ethylsulfonyl)diazomethane, bis(1-methylpropylsulfonyl)diazomethane, bis(2-methylpropylsulfonyl)diazomethane, bis(1,1-dimethylethylsulfonyl)diazomethane, bis(cyclohexylsulfonyl)diazomethane, bis(perfluoroisopropylsulfonyl)diazomethane, bis(phenylsulfonyl)diazomethane, bis(4-methylphenylsulfonyl)diazomethane, bis(2,4-dimethylphenylsulfonyl)diazomethane, bis(2-naphthylsulfonyl)diazomethane, bis(4-acetyloxyphenylsulfonyl)diazomethane, bis(4-methanesulfonyloxyphenylsulfonyl)diazomethane, bis(4-(4-toluenesulfonyloxy)phenylsulfonyl)diazomethane, bis(4-(n-hexyloxy)phenylsulfonyl)diazomethane, bis(2-methyl-4-(n-hexyloxy)phenylsulfonyl)diazomethane, bis(2,5-dimethyl-4-(n-hexyloxy)phenylsulfonyl)diazomethane, bis(3,5-dimethyl-4-(n-hexyloxy)phenylsulfonyl)diazomethane, bis (2-methyl-5-isopropyl-4-(n-hexyloxy)phenylsulfonyl)-diazomethane, 4-methylphenylsulfonylbenzoyldiazomethane, tert-butylcarbonyl-4-methylphenylsulfonyldiazomethane, 2-naphthylsulfonylbenzoyldiazomethane, 4-methylphenylsulfonyl-2-naphthoyldiazomethane, methylsulfonylbenzoyldiazomethane, and tert-butoxycarbonyl-4-methylphenylsulfonyldiazomethane.

N-sulfonyloxyimide photoacid generators include combinations of imide skeletons with sulfonates. Exemplary imide skeletons are succinimide, naphthalene dicarboxylic acid imide, phthalimide, cyclohexyldicarboxylic acid imide, 5-norbornene-2,3-dicarboxylic acid imide, and 7-oxabicyclo [2.2.1]-5-heptene-2,3-dicarboxylic acid imide. Exemplary sulfonates include trifluoromethanesulfonate, nonafluorobutanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, naphthalenesulfonate, camphorsulfonate, octanesulfonate, dodecylbenzenesulfonate, butanesulfonate, and methanesulfonate.

Benzoinsulfonate photoacid generators include benzoin tosylate, benzoin mesylate, and benzoin butanesulfonate.

Pyrogallol trisulfonate photoacid generators include pyrogallol, fluoroglycine, catechol, resorcinol, and hydroquinone, in which all the hydroxyl groups are substituted with trifluoromethanesulfonate, nonafluorobutanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, toluenesulfonate, benzenesulfonate, naphthalenesulfonate, camphorsulfonate, octanesulfonate, dodecylbenzenesulfonate, butanesulfonate, and methanesulfonate.

Nitrobenzyl sulfonate photoacid generators include 2,4-dinitrobenzyl sulfonate, 2-nitrobenzyl sulfonate, and 2,6-dinitrobenzyl sulfonate, with exemplary sulfonates including trifluoromethanesulfonate, nonafluorobutanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, toluenesulfonate, benzenesulfonate, naphthalenesulfonate, camphorsulfonate, octanesulfonate, dodecylbenzenesulfonate, butanesulfonate, and methanesulfonate. Also useful are analogous nitrobenzyl sulfonate compounds in which the nitro group on the benzyl side is substituted with a trifluoromethyl group.

Sulfone photoacid generators include bis(phenylsulfonyl)methane, bis(4-methylphenylsulfonyl)methane, bis(2-naphthylsulfonyl)methane, 2,2-bis(phenylsulfonyl)propane, 2,2-bis(4-methylphenylsulfonyl)propane, 2,2-bis(2-naphthylsulfonyl)propane, 2-methyl-2-(p-toluenesulfonyl)propiophenone, 2-cyclohexylcarbonyl-2-(p-toluenesulfonyl)propane, and 2,4-dimethyl-2-(p-toluenesulfonyl)pentan-3-one.

Photoacid generators in the form of glyoxime derivatives are described in Japanese Patent No. 2,906,999 and JP-A 9-301948 and include bis-O-(p-toluenesulfonyl)-α-dimethylglyoxime, bis-O-(p-toluenesulfonyl)-α-diphenylglyoxime, bis-O-(p-toluenesulfonyl)-α-dicyclohexylglyoxime, bis-O-(p-toluenesulfonyl)-2,3-pentanedioneglyoxime, bis-O-(n-butanesulfonyl)-α-dimethylglyoxime, bis-O-(n-butanesulfonyl)-α-diphenylglyoxime, bis-O-(n-butanesulfonyl)-α-dicyclohexylglyoxime, bis-O-(methanesulfonyl)-α-dimethylglyoxime, bis-O-(trifluoromethanesulfonyl)-α-dimethylglyoxime, bis-O-(2,2,2-trifluoroethanesulfonyl)-α-dimethylglyoxime, bis-O-(10-camphorsulfonyl)-α-dimethylglyoxime, bis-O-(benzenesulfonyl)-α-dimethylglyoxime, bis-O-(p-fluorobenzenesulfonyl)-α-dimethylglyoxime, bis-O-(p-trifluoromethylbenzenesulfonyl)-α-dimethylglyoxime, bis-O-(xylenesulfonyl)-α-dimethylglyoxime, bis-O-(trifluoromethanesulfonyl)-nioxime, bis-O-(2,2,2-trifluoroethanesulfonyl)-nioxime, bis-O-(10-camphorsulfonyl)-nioxime, bis-O-(benzenesulfonyl)-nioxime, bis-O-(p-fluorobenzenesulfonyl)-nioxime, bis-O-(p-trifluoromethylbenzenesulfonyl)-nioxime, and bis-O-(xylenesulfonyl)-nioxime.

Also included are the oxime sulfonates described in U.S. Pat. No. 6,004,724, for example, (5-(4-toluenesulfonyl)oxyimino-5H-thiophen-2-ylidene)phenyl-acetonitrile, (5-(10-camphorsulfonyl)oxyimino-5H-thiophen-2-ylidene)phenyl-acetonitrile, (5-n-octanesulfonyloxyimino-5H-thiophen-2-ylidene)phenyl-acetonitrile, (5-(4-toluenesulfonyl)oxyimino-5H-thiophen-2-ylidene)(2-methylphenyl)acetonitrile, (5-(10-camphorsulfonyl)oxyimino-5H-thiophen-2-ylidene)(2-methylphenyl)acetonitrile, (5-n-octanesulfonyloxyimino-5H-thiophen-2-ylidene)(2-methylphenyl)acetonitrile, etc.

Also included are the oxime sulfonates described in U.S. Pat. No. 6,261,738 and JP-A 2000-314956, for example, 2,2,2-trifluoro-1-phenyl-ethanone oxime-O-methylsulfonate;
2,2,2-trifluoro-1-phenyl-ethanone oxime-O-(10-camphorylsulfonate);
2,2,2-trifluoro-1-phenyl-ethanone oxime-O-(4-methoxyphenylsulfonate);
2,2,2-trifluoro-1-phenyl-ethanone oxime-O-(1-naphthylsulfonate);
2,2,2-trifluoro-1-phenyl-ethanone oxime-O-(2-naphthylsulfonate);
2,2,2-trifluoro-1-phenyl-ethanone oxime-O-(2,4,6-trimethylphenylsulfonate);
2,2,2-trifluoro-1-(4-methylphenyl)-ethanone oxime-O-(10-camphorylsulfonate);
2,2,2-trifluoro-1-(4-methylphenyl)-ethanone oxime-O-(methylsulfonate);
2,2,2-trifluoro-1-(2-methylphenyl)-ethanone oxime-O-(10-camphorylsulfonate);
2,2,2-trifluoro-1-(2,4-dimethylphenyl)-ethanone oxime-O-(10-camphorylsulfonate);
2,2,2-trifluoro-1-(2,4-dimethylphenyl)-ethanone oxime-O-(1-naphthylsulfonate);
2,2,2-trifluoro-1-(2,4-dimethylphenyl)-ethanone oxime-O-(2-naphthylsulfonate);
2,2,2-trifluoro-1-(2,4,6-trimethylphenyl)-ethanone oxime-O-(10-camphorylsulfonate);
2,2,2-trifluoro-1-(2,4,6-trimethylphenyl)-ethanone oxime-O-(1-naphthylsulfonate);
2,2,2-trifluoro-1-(2,4,6-trimethylphenyl)-ethanone oxime-O-(2-naphthylsulfonate);
2,2,2-trifluoro-1-(4-methoxyphenyl)-ethanone oxime-O-methylsulfonate;
2,2,2-trifluoro-1-(4-methylthiophenyl)-ethanone oxime-O-methylsulfonate;
2,2,2-trifluoro-1-(3,4-dimethoxyphenyl)-ethanone oxime-O-methylsulfonate;
2,2,3,3,4,4,4-heptafluoro-1-phenyl-butanone oxime-O-(10-camphorylsulfonate);
2,2,2-trifluoro-1-(phenyl)-ethanone oxime-O-methylsulfonate;
2,2,2-trifluoro-1-(phenyl)-ethanone oxime-O-10-camphorylsulfonate;
2,2,2-trifluoro-1-(phenyl)-ethanone oxime-O-(4-methoxyphenyl)sulfonate;
2,2,2-trifluoro-1-(phenyl)-ethanone oxime-O-(1-naphthyl)sulfonate;
2,2,2-trifluoro-1-(phenyl)-ethanone oxime-O-(2-naphthyl)sulfonate;
2,2,2-trifluoro-1-(phenyl)-ethanone oxime-O-(2,4,6-trimethylphenyl)sulfonate;
2,2,2-trifluoro-1-(4-methylphenyl)-ethanone oxime-O-(10-camphoryl)sulfonate;
2,2,2-trifluoro-1-(4-methylphenyl)-ethanone oxime-O-methylsulfonate;
2,2,2-trifluoro-1-(2-methylphenyl)-ethanone oxime-O-(10-camphoryl)sulfonate;
2,2,2-trifluoro-1-(2,4-dimethylphenyl)-ethanone oxime-O-(1-naphthyl)sulfonate;
2,2,2-trifluoro-1-(2,4-dimethylphenyl)-ethanone oxime-O-(2-naphthyl)sulfonate;
2,2,2-trifluoro-1-(2,4,6-trimethylphenyl)-ethanone oxime-O-(10-camphoryl)sulfonate;
2,2,2-trifluoro-1-(2,4,6-trimethylphenyl)-ethanone oxime-O-(1-naphthyl)sulfonate;
2,2,2-trifluoro-1-(2,4,6-trimethylphenyl)-ethanone oxime-O-(2-naphthyl)sulfonate;
2,2,2-trifluoro-1-(4-methoxyphenyl)-ethanone oxime-O-methylsulfonate;
2,2,2-trifluoro-1-(4-thiomethylphenyl)-ethanone oxime-O-methylsulfonate;
2,2,2-trifluoro-1-(3,4-dimethoxyphenyl)-ethanone oxime-O-methylsulfonate;
2,2,2-trifluoro-1-(4-methoxyphenyl)-ethanone oxime-O-(4-methylphenyl)sulfonate;

2,2,2-trifluoro-1-(4-methoxyphenyl)-ethanone oxime-O-(4-methoxyphenyl)sulfonate;
2,2,2-trifluoro-1-(4-methoxyphenyl)-ethanone oxime-O-(4-dodecylphenyl)sulfonate;
2,2,2-trifluoro-1-(4-methoxyphenyl)-ethanone oxime-O-octylsulfonate;
2,2,2-trifluoro-1-(4-thiomethylphenyl)-ethanone oxime-O-(4-methoxyphenyl)sulfonate;
2,2,2-trifluoro-1-(4-thiomethylphenyl)-ethanone oxime-O-(4-dodecylphenyl)sulfonate;
2,2,2-trifluoro-1-(4-thiomethylphenyl)-ethanone oxime-O-octylsulfonate;
2,2,2-trifluoro-1-(4-thiomethylphenyl)-ethanone oxime-O-(2-naphthyl)sulfonate;
2,2,2-trifluoro-1-(2-methylphenyl)-ethanone oxime-O-methylsulfonate;
2,2,2-trifluoro-1-(4-methylphenyl)ethanone oxime-O-phenylsulfonate;
2,2,2-trifluoro-1-(4-chlorophenyl)-ethanone oxime-O-phenylsulfonate;
2,2,3,3,4,4,4-heptafluoro-1-(phenyl)-butanone oxime-O-(10-camphoryl)sulfonate;
2,2,2-trifluoro-1-naphthyl-ethanone oxime-O-methylsulfonate;
2,2,2-trifluoro-2-naphthyl-ethanone oxime-O-methylsulfonate;
2,2,2-trifluoro-1-[4-benzylphenyl]-ethanone oxime-O-methylsulfonate;
2,2,2-trifluoro-1-[4-(phenyl-1,4-dioxa-but-1-yl)phenyl]-ethanone oxime-O-methylsulfonate;
2,2,2-trifluoro-1-naphthyl-ethanone oxime-O-propylsulfonate;
2,2,2-trifluoro-2-naphthyl-ethanone oxime-O-propylsulfonate;
2,2,2-trifluoro-1-[4-benzylphenyl]-ethanone oxime-O-propylsulfonate;
2,2,2-trifluoro-1-[4-methylsulfonylphenyl]-ethanone oxime-O-propylsulfonate;
1,3-bis[1-(4-phenoxyphenyl)-2,2,2-trifluoroethanone oxime-O-sulfonyl]phenyl;
2,2,2-trifluoro-1-[4-methylsulfonyloxyphenyl]-ethanone oxime-O-propylsulfonate;
2,2,2-trifluoro-1-[4-methylcarbonyloxyphenyl]-ethanone oxime-O-propylsulfonate;
2,2,2-trifluoro-1-[6H,7H-5,8-dioxonaphth-2-yl]-ethanone oxime-O-propylsulfonate;
2,2,2-trifluoro-1-[4-methoxycarbonylmethoxyphenyl]-ethanone oxime-O-propylsulfonate;
2,2,2-trifluoro-1-[4-(methoxycarbonyl)-(4-amino-1-oxa-pent-1-yl)-phenyl]-ethanone oxime-O-propylsulfonate;
2,2,2-trifluoro-1-[3,5-dimethyl-4-ethoxyphenyl]-ethanone oxime-O-propylsulfonate;
2,2,2-trifluoro-1-[4-benzyloxyphenyl]-ethanone oxime-O-propylsulfonate;
2,2,2-trifluoro-1-[2-thiophenyl]-ethanone oxime-O-propylsulfonate; and
2,2,2-trifluoro-1-[1-dioxa-thiophen-2-yl)]-ethanone oxime-O-propylsulfonate.

Also included are the oxime sulfonates described in JP-A 9-95479 and JP-A 9-230588 and the references cited therein, for example,
α-(p-toluenesulfonyloxyimino)-phenylacetonitrile,
α-(p-chlorobenzenesulfonyloxyimino)-phenylacetonitrile,
α-(4-nitrobenzenesulfonyloxyimino)-phenylacetonitrile,
α-(4-nitro-2-trifluoromethylbenzenesulfonyloxyimino)-phenylacetonitrile,
α-(benzenesulfonyloxyimino)-4-chlorophenylacetonitrile,
α-(benzenesulfonyloxyimino)-2,4-dichlorophenylacetonitrile,
α-(benzenesulfonyloxyimino)-2,6-dichlorophenylacetonitrile,
α-(benzenesulfonyloxyimino)-4-methoxyphenylacetonitrile,
α-(2-chlorobenzenesulfonyloxyimino)-4-methoxyphenylacetonitrile,
α-(benzenesulfonyloxyimino)-2-thienylacetonitrile,
α-(4-dodecylbenzenesulfonyloxyimino)-phenylacetonitrile,
α-[(4-toluenesulfonyloxyimino)-4-methoxyphenyl]acetonitrile,
α-[(dodecylbenzenesulfonyloxyimino)-4-methoxyphenyl]-acetonitrile,
α-(tosyloxyimino)-3-thienylacetonitrile,
α-(methylsulfonyloxyimino)-1-cyclopentenylacetonitrile,
α-(ethylsulfonyloxyimino)-1-cyclopentenylacetonitrile,
α-(isopropylsulfonyloxyimino)-1-cyclopentenylacetonitrile,
α-(n-butylsulfonyloxyimino)-1-cyclopentenylacetonitrile,
α-(ethylsulfonyloxyimino)-1-cyclohexenylacetonitrile,
α-(isopropylsulfonyloxyimino)-1-cyclohexenylacetonitrile, and
α-(n-butylsulfonyloxyimino)-1-cyclohexenylacetonitrile.

Suitable bisoxime sulfonates include those described in JP-A 9-208554, for example,
bis(α-(4-toluenesulfonyloxy)imino)-p-phenylenediacetonitrile,
bis(α-(benzenesulfonyloxy)imino)-p-phenylenediacetonitrile,
bis(α-(methanesulfonyloxy)imino)-p-phenylenediacetonitrile,
bis(α-(butanesulfonyloxy)imino)-p-phenylenediacetonitrile,
bis(α-(10-camphorsulfonyloxy)imino)-p-phenylenediacetonitrile,
bis(α-(4-toluenesulfonyloxy)imino)-p-phenylenediacetonitrile,
bis(α-(trifluoromethanesulfonyloxy)imino)-p-phenylenediacetonitrile,
bis(α-(4-methoxybenzenesulfonyloxy)imino)-p-phenylenediacetonitrile,
bis(α-(4-toluenesulfonyloxy)imino)-m-phenylenediacetonitrile,
bis(α-(benzenesulfonyloxy)imino)-m-phenylenediacetonitrile,
bis(α-(methanesulfonyloxy)imino)-m-phenylenediacetonitrile,
bis(α-(butanesulfonyloxy)imino)-m-phenylenediacetonitrile,
bis(α-(10-camphorsulfonyloxy)imino)-m-phenylenediacetonitrile,
bis(α-(4-toluenesulfonyloxy)imino)-m-phenylenediacetonitrile,
bis(α-(trifluoromethanesulfonyloxy)imino)-m-phenylenediacetonitrile,
bis(α-(4-methoxybenzenesulfonyloxy)imino)-m-phenylenediacetonitrile, etc.

Of these, preferred photoacid generators are sulfonium salts, bissulfonyldiazomethanes, N-sulfonyloxyimides and glyoxime derivatives. More preferred photoacid generators are sulfonium salts, bissulfonyldiazomethanes, and N-sulfonyloxyimides. Typical examples include
triphenylsulfonium p-toluenesulfonate,
triphenylsulfonium camphorsulfonate,
triphenylsulfonium pentafluorobenzenesulfonate,
triphenylsulfonium nonafluorobutanesulfonate, triphenylsulfonium 4-(4'-toluenesulfonyloxy)benzenesulfonate,
triphenylsulfonium 2,4,6-triisopropylbenzenesulfonate,
4-tert-butoxyphenyldiphenylsulfonium p-toluenesulfonate,
4-tert-butoxyphenyldiphenylsulfonium camphorsulfonate,
4-tert-butoxyphenyldiphenylsulfonium 4-(4'-toluenesulfonyloxy)benzenesulfonate,
tris(4-methylphenyl)sulfonium camphorsulfonate,
tris(4-tert-butylphenyl)sulfonium camphorsulfonate,
bis(tert-butylsulfonyl)diazomethane,
bis(cyclohexylsulfonyl)diazomethane,
bis(2,4-dimethylphenylsulfonyl)diazomethane,
bis(4-(n-hexyloxy)phenylsulfonyl)diazomethane,
bis(2-methyl-4-(n-hexyloxy)phenylsulfonyl)diazomethane,
bis(2,5-dimethyl-4-(n-hexyloxy)phenylsulfonyl)diazomethane,
bis(3,5-dimethyl-4-(n-hexyloxy)phenylsulfonyl)diazomethane,
bis(2-methyl-5-isopropyl-4-(n-hexyloxy)phenylsulfonyl)diazomethane,
bis(4-tert-butylphenylsulfonyl)diazomethane, N-camphorsulfonyloxy-5-norbornene-2,3-dicarboxylic acid imide, and N-p-toluenesulfonyloxy-5-norbornene-2,3-dicarboxylic acid imide.

In the chemically amplified resist composition, an appropriate amount of the photoacid generator is, but not limited to, 0.1 to 10 parts, and especially 0.1 to 5 parts by weight per 100 parts by weight of the base resin. Too high a proportion of the photoacid generator may give rise to problems of degraded resolution and foreign matter upon development and resist film peeling. The photoacid generators may be used alone or in admixture of two or more. The transmittance of the resist film can be controlled by using a photoacid generator having a low transmittance at the exposure wavelength and adjusting the amount of the photoacid generator added.

In the resist composition, there may be added a compound which is decomposed with an acid to generate an acid, that is, acid-amplifier compound. For these compounds, reference should be made to J. Photopolym. Sci. and Tech., 8, 43-44, 45-46 (1995), and ibid., 9, 29-30 (1996).

Examples of the acid-amplifier compound include tert-butyl-2-methyl-2-tosyloxymethyl acetoacetate and 2-phenyl-2-(2-tosyloxyethyl)-1,3-dioxolane, but are not limited thereto. Of well-known photoacid generators, many of those compounds having poor stability, especially poor thermal stability exhibit an acid amplifier-like behavior.

In the resist composition, an appropriate amount of the acid-amplifier compound is up to 2 parts, and especially up to 1 part by weight per 100 parts by weight of the base resin. Excessive amounts of the acid-amplifier compound make diffusion control difficult, leading to degradation of resolution and pattern profile.

In addition to the inventive nitrogen-containing organic compound, one or more of commonly used nitrogen-containing organic compounds may be employed in the inventive resist composition.

In addition to the above components, the inventive resist composition may optionally include known additives such as dissolution regulators, surfactants, acidic compounds, dyes, thermal crosslinkers, acid crosslinkers, and stabilizers.

Pattern formation using the resist composition of the invention may be carried out by a known lithographic technique. For example, the resist composition may be applied onto a substrate such as a silicon wafer by spin coating or the like to form a resist film having a thickness of 0.05 to 2.0 μm, which is then pre-baked on a hot plate at 60 to 150° C. for 0.1 to 10 minutes, and preferably at 80 to 140° C. for 0.5 to 5 minutes. A patterning mask having the desired pattern may then be placed over the resist film, and the film exposed through the mask to an electron beam or to high-energy radiation such as deep-UV rays, excimer laser beams, or x-rays in a dose of about 1 to 200 mJ/cm$^2$, and preferably about 10 to 100 mJ/cm$^2$. Light exposure may be done by a conventional exposure process or in some cases, by an immersion process of providing liquid impregnation between the mask and the resist. The resist film is then post-exposure baked (PEB) on a hot plate at 60 to 150° C. for 0.1 to 5 minutes, and preferably at 80 to 140° C. for 0.5 to 3 minutes. Finally, development may be carried out using as the developer an aqueous alkali solution, such as 0.1 to 5 wt %, and preferably 2 to 3 wt %, tetramethylammonium hydroxide (TMAH), this being done by a conventional method such as dip, puddle, or spray technique for a period of 0.1 to 3 minutes, and preferably 0.5 to 2 minutes. These steps result in the formation of the desired pattern on the substrate. If necessary, the pattern as developed can be heat treated for adjusting the pattern size (known as the thermal flow process).

Of the various types of high-energy radiation that may be used, the resist composition of the invention is best suited to micro-pattern formation with, in particular, deep-UV rays having a wavelength of 250 to 120 nm or excimer laser beams, extremely short UV, x-rays or electron beams.

EXAMPLE

Examples of the invention are given below by way of illustration and not by way of limitation. The meaning of abbreviations is Me for methyl, and Ac for acetyl.

Synthesis Examples

Nitrogen-containing organic compounds within the scope of the invention were synthesized by the method described below.

Synthesis Example 1

Synthesis of nitrilotriethane-2,1-diyl tris(7-oxanorbornane-2-carboxylate) (Amine 1)

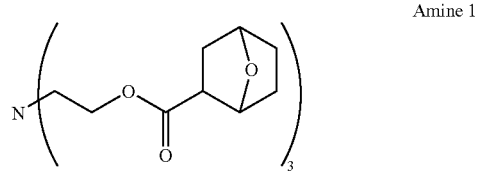

Amine 1

To a mixture of 149 g of triethanolamine, 405 g of triethylamine, and 1,500 g of methylene chloride at 5-10° C., 506 g of 7-oxanorbornane-2-carboxylic chloride was added dropwise over 2 hours. The mixture was then stirred for 10 hours at 25° C. Water was added to the reaction mixture to stop the reaction, followed by conventional aqueous work-up and purification by column chromatography. There was obtained 469 g of nitrilotriethane-2,1-diyl tris(7-oxanorbornane-2-carboxylate) (yield 90%).

Synthesis Example 2

Synthesis of nitrilotripropane-1,2-diyl tris(7-oxanorbornane-2-carboxylate) (Amine 2)

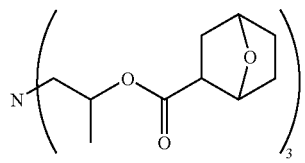

Amine 2

By following the procedure of Synthesis Example 1 aside from using an equimolar amount of triisopropanolamine instead of the triethanolamine, nitrilotripropane-1,2-diyl tris (7-oxanorbornane-2-carboxylate) was synthesized (yield 87%).

Synthesis Example 3

Synthesis of N-methylnitrilodiethane-2,1-diyl bis(7-oxanorbornane-2-carboxylate) (Amine 3)

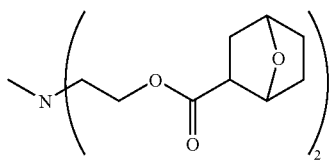

Amine 3

A mixture of 119 g of methyldiethanolamine, 344 g of methyl 7-oxanorbornane-2-carboxylate, 1.0 g of sodium methoxide and 400 g of toluene was heated under reflux for 10 hours while distilling off the methanol resulting from reaction. The reaction mixture was concentrated and then purified by distillation at reduced pressure, to give 276 g of N-methylnitrilodiethane-2,1-diyl bis(7-oxanorbornane-2-carboxylate) (boiling point 187° C./11 Pa, yield 75%).

IR (KBr): $\nu$=2981, 2956, 2877, 2848, 2796, 1733, 1467, 1454, 1392, 1346, 1307, 1272, 1180, 1062, 1039, 1027, 1002, 929 cm$^{-1}$ $^1$H-NMR of major isomer (600 MHz in CDCl$_3$): $\delta$=1.40-1.80 (10H, m), 2.10 (2H, m), 2.32 (3H, s), 2.60 (2H, m), 2.68 (4H, m), 4.17 (4H, m), 4.63 (2H, br. t, J=5.0 Hz), 4.78 (2H, Br. d, J=5.1 Hz)

Synthesis Example 4

Synthesis of N-butylnitrilodiethane-2,1-diyl bis(7-oxanorbornane-2-carboxylate) (Amine 4)

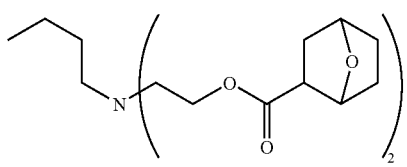

Amine 4

By following the procedure of Synthesis Example 3 aside from using an equimolar amount of butyldiethanolamine instead of the methyldiethanolamine, N-butylnitrilodiethane-2,1-diyl bis(7-oxanorbornane-2-carboxylate) was synthesized (boiling point 204° C./15 Pa, yield 73%).

IR (KBr): $\nu$=2956, 2873, 2823, 1735, 1467, 1456, 1376, 1346, 1307, 1270, 1180, 1062, 1025, 1002, 929 cm$^{-1}$ $^1$H-NMR of major isomer (600 MHz in CDCl$_3$): $\delta$=0.89 (3H, t, J=7.4 Hz), 1.28 (2H, tq, J=7.5, 7.4 Hz), 1.35-1.80 (12H, m), 2.11 (2H, m), 2.50 (2H, t, J=7.6 Hz), 2.59 (2H, dd, J=9.3, 4.8 Hz), 2.75 (4H, t, J=6.2 Hz), 4.12 (4H, t, J=6.2 Hz), 4.64 (2H, m), 4.80 (2H, br. d, J=4.8 Hz)

Synthesis Example 5

Synthesis of N-phenylnitrilodiethane-2,1-diyl bis(7-oxanorbornane-2-carboxylate) (Amine 5)

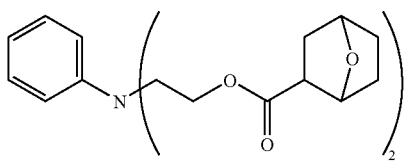

Amine 5

By following the procedure of Synthesis Example 3 aside from using an equimolar amount of phenyldiethanolamine instead of the methyldiethanolamine and purifying the product by column chromatography, N-phenylnitrilodiethane-2,1-diyl bis(7-oxanorbornane-2-carboxylate) was synthesized (yield 83%).

Synthesis Example 6

Synthesis of N-(2-methoxyethyl)nitrilodiethane-2,1-diyl bis(7-oxanorbornane-2-carboxylate) (Amine 6)

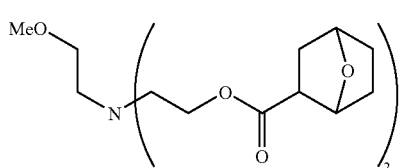

Amine 6

With stirring and ice cooling, 96.9 g of ethylene oxide was added to a mixture of 75.1 g of 2-methoxyethylamine and 150 g of water. The mixture was slowly warmed up to room temperature and stirred for 20 hours. The reaction mixture was concentrated and distilled at reduced pressure, to give N-(2-methoxyethyl)diethanolamine. By following the procedure of Synthesis Example 3 aside from using this amine instead of the methyldiethanolamine, 288 g of N-(2-methoxyethyl)nitrile-diethane-2,1-diyl bis(7-oxanorbornane-2-carboxylate) was obtained (boiling point 212° C./23 Pa, yield 70%).

IR (KBr): $\nu$=2981, 2956, 2875, 2829, 1733, 1454, 1346, 1307, 1270, 1182, 1120, 1062, 1002, 929 cm$^{-1}$ $^1$H-NMR of major isomer (600 MHz in CDCl$_3$): $\delta$=1.40-1.60 (10H, m), 2.10 (2H, m), 2.59 (2H, dd, J=8.9, 4.8 Hz), 2.76 (2H, d, J=5.8 Hz), 2.83 (4H, t, J=6.2 Hz), 3.32 (3H, s), 3.42 (2H, t, J=5.8 Hz), 4.13 (4H, t, J=6.2 Hz), 4.63 (2H, m), 4.79 (2H, br. d, J=4.5 Hz)

Synthesis Example 7

Synthesis of N-(2-cyanoethyl)nitrilodiethane-2,1-diyl bis(7-oxanorbornane-2-carboxylate) (Amine 7)

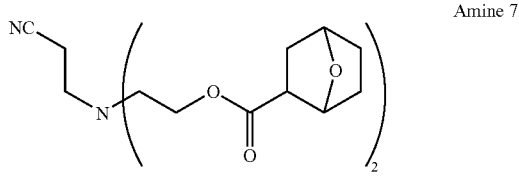

Amine 7

By following the procedure of Synthesis Example 1 aside from using N-(2-cyanoethyl)nitrilodiethanol instead of the triethanolamine, N-(2-cyanoethyl)nitrilodiethane-2,1-diyl bis(7-oxanorbornane-2-carboxylate) was synthesized (yield 85%).

Synthesis Example 8

Synthesis of N,N-bis(2-acetoxyethyl)nitriloethane-2,1-diyl 7-oxanorbornane-2-carboxylate (Amine 8)

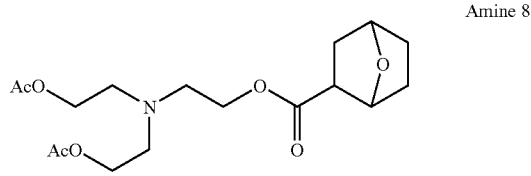

Amine 8

By following the procedure of Synthesis Example 1 aside from using N-(2-hydroxyethyl)nitrilodiethane-2,1-diyl diacetate instead of the triethanolamine, N,N-bis(2-acetoxyethyl)nitriloethane-2,1-diyl 7-oxanorbornane-2-carboxylate was synthesized (boiling point 166° C./12 Pa, yield 93%).

IR (KBr): ν=2958, 2879, 2836, 1737, 1454, 1371, 1307, 1236, 1182, 1041, 1002, 929 cm$^{-1}$ $^1$H-NMR of major isomer (600 MHz in CDCl$_3$): δ=1.40-1.80 (5H, m), 2.03 (6H, s), 2.10 (1H, m), 2.59 (1H, dd, J=8.9, 4.8 Hz), 2.75-2.90 (6H, m), 4.09 (4H, t, J=6.0 Hz), 4.12 (2H, t, J=6.0 Hz), 4.63 (1H, br. t, J=5.2 Hz), 4.78 (1H, br. d, J=5.2 Hz)

Synthesis Example 9

Synthesis of N,N-bis(2-methoxyethyl)nitriloethane-2,1-diyl 7-oxanorbornane-2-carboxylate (Amine 9)

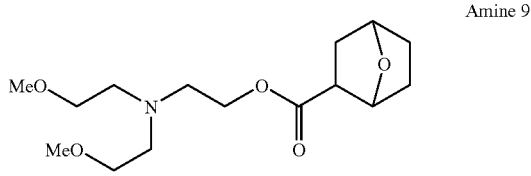

Amine 9

By following the procedure of Synthesis Example 6 aside from using bis(2-methoxyethyl)amine instead of the 2-methoxyethylamine, N,N-bis(2-methoxyethyl)nitriloethane-2,1-diyl 7-oxanorbornane-2-carboxylate was synthesized (boiling point 131° C./11 Pa, yield 75%).

IR (KBr): ν=2979, 2954, 2875, 2817, 1735, 1454, 1346, 1307, 1270, 1184, 1120, 1074, 1064, 1002, 929 cm$^{-1}$ $^1$H-NMR of major isomer (600 MHz in CDCl$_3$): δ=1.40-1.75 (5H, m), 2.08 (1H, m), 2.56 (1H, dd, J=9.3, 4.8 Hz), 2.74 (4H, t, J=5.8 Hz), 2.81 (2H, m), 3.29 (6H, s), 3.41 (4H, t, J=5.8 Hz), 4.13 (2H, t, J=6.0 Hz), 4.61 (1H, br. t, J=5.2 Hz), 4.77 (1H, br. d, J=4.8 Hz)

Synthesis Example 10

Synthesis of 2-piperidinoethyl 7-oxanorbornane-2-carboxylate (Amine 10)

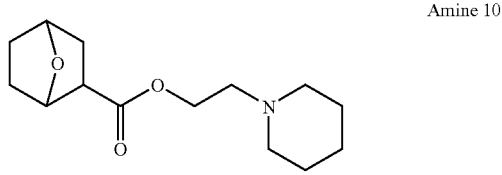

Amine 10

By following the procedure of Synthesis Example 3 aside from using 2-piperidinoethanol instead of the methyldiethanolamine, 2-piperidinoethyl 7-oxanorbornane-2-carboxylate was synthesized (yield 86%).

Synthesis Example 11

Synthesis of 2-morpholinoethyl 7-oxanorbornane-2-carboxylate (Amine 11)

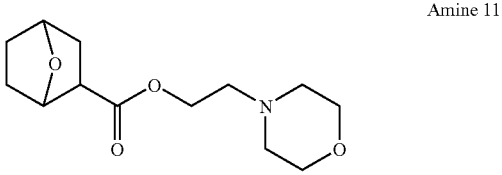

Amine 11

By following the procedure of Synthesis Example 3 aside from using 2-morpholinoethanol instead of the methyldiethanolamine, 2-morpholinoethyl 7-oxanorbornane-2-carboxylate was synthesized (boiling point 119° C./8 Pa, yield 84%).

IR (KBr): ν=2956, 2892, 2854, 2805, 2692, 1735, 1454, 1407, 1371 1346, 1305, 1272, 1187, 1160, 1118, 1062, 1035, 1024, 1002, 981, 943, 927, 916, 860 cm$^{-1}$ $^1$H-NMR of major isomer (600 MHz in CDCl$_3$): δ=1.40-1.55 (2H, m), 1.60-1.75 {3H, m including 1.67 (1H, dd, J=12.0, 8.9 Hz)}, 2.09 (1H, m), 2.46 (4H, m), 2.55-2.60 (3H, m), 3.65 (4H, m), 4.10-4.25 (2H, m), 4.62 (1H, br. t, J=5.2 Hz), 4.77 (1H, br. d, J=5.2 Hz)

Synthesis Example 12

Synthesis of 2-(1H-imidazol-1-yl)ethyl 7-oxanorbornane-2-carboxylate (Amine 12)

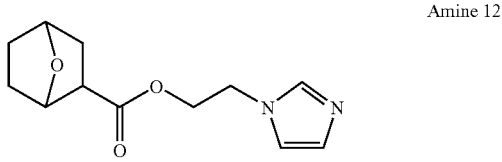

Amine 12

By following the procedure of Synthesis Example 1 aside from using 2-(1H-imidazol-1-yl)ethanol instead of the triethanolamine, 2-(1H-imidazol-1-yl)ethyl 7-oxanorbornane-2-carboxylate was synthesized (yield 74%).

Synthesis Example 13

Synthesis of 2-(1H-benzimidazol-1-yl)ethyl 7-oxanorbornane-2-carboxylate (Amine 13)

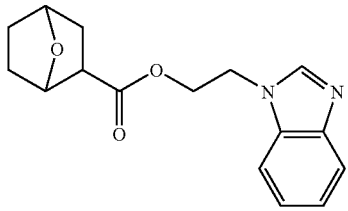

Amine 13

By following the procedure of Synthesis Example 1 aside from using 2-(1H-benzimidazol-1-yl)ethanol instead of the triethanolamine, 2-(1H-benzimidazol-1-yl)ethyl 7-oxanorbornane-2-carboxylate was synthesized (yield 80%).

Synthesis Example 14

Synthesis of 2-(2-oxo-1-pyrrolidinyl)ethyl 7-oxanorbornane-2-carboxylate (Amine 14)

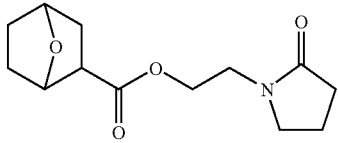

Amine 14

By following the procedure of Synthesis Example 1 aside from using 2-(2-oxo-1-pyrrolidinyl)ethanol instead of the triethanolamine, 2-(2-oxo-1-pyrrolidinyl)ethyl 7-oxanorbornane-2-carboxylate was synthesized (yield 81%).

Synthesis Example 15

Synthesis of piperazine-1,4-diyldiethane-2,1-diyl bis(7-oxanorbornane-2-carboxylate) (Amine 15)

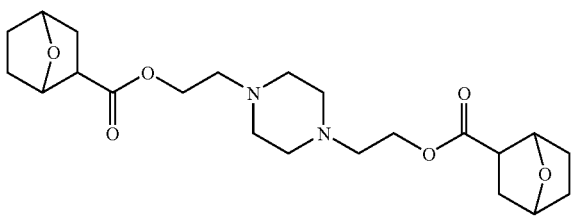

Amine 15

By following the procedure of Synthesis Example 3 aside from using 1,4-bis(2-hydroxyethyl)piperazine instead of the methyldiethanolamine and purifying the product by column chromatography, piperazine-1,4-diyldiethane-2,1-diyl bis(7-oxanorbornane-2-carboxylate) was synthesized (yield 68%).

EXAMPLES

Resist compositions were prepared by using nitrogen-containing organic compounds of the invention, and evaluated for resolution and pattern profile by carrying out the patterning process of the invention.

The base polymer (Polymers 1 to 14), photoacid generator (PAG1 to 5), resolution regulator (DRI) and crosslinker used in Examples are identified below by their structural formula. Note that PGMEA is propylene glycol monomethyl ether acetate. Weight and number average molecular weights, Mw and Mn, are determined by gel permeation chromatography (GPC) using polystyrene standards.

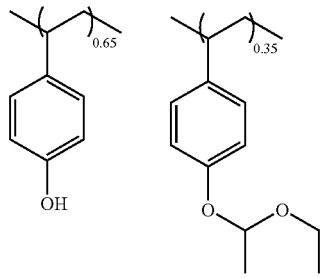

Polymer 1
Mw 10,000
Mw/Mn 1.10

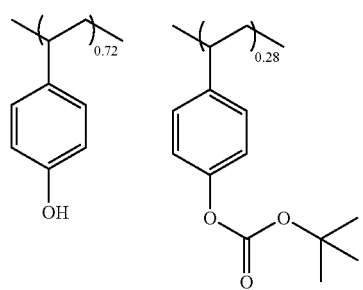

Polymer 2
Mw 10,000
Mw/Mn 1.10

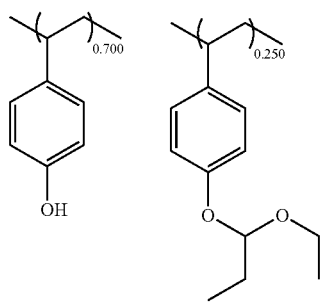

-continued
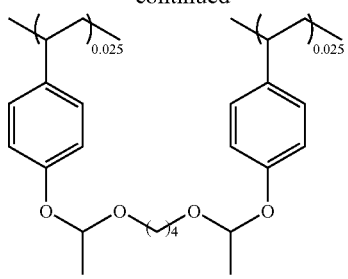
Polymer 3
Mw 16,000
Mw/Mn 1.60
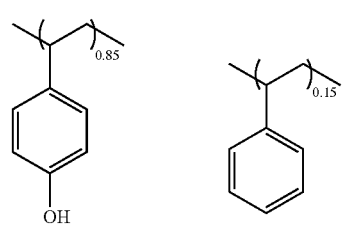
Polymer 4
Mw 10,000
Mw/Mn 1.10
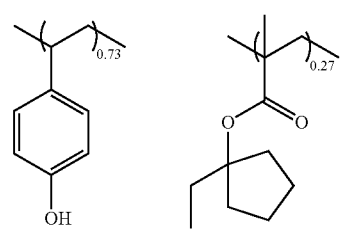
Polymer 5
Mw 12,000
Mw/Mn 1.60
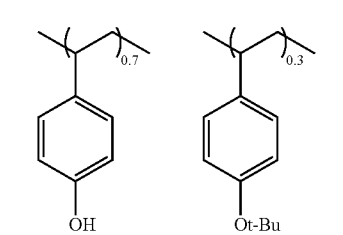
Polymer 6
Mw 8,000
Mw/Mn 1.10
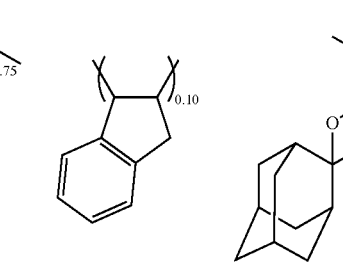
Polymer 7
Mw 8,000
Mw/Mn 1.80
-continued
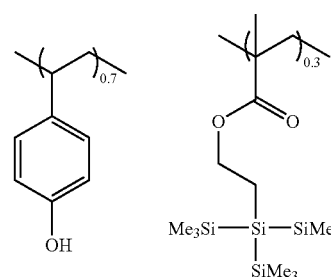
Polymer 8
Mw 10,000
Mw/Mn 1.72
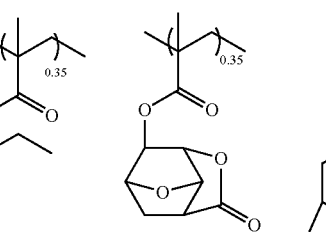
Polymer 9
Mw 8,000
Mw/Mn 1.90
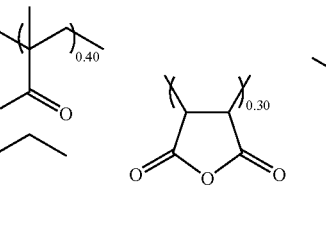
Polymer 10
Mw 9,000
Mw/Mn 1.90
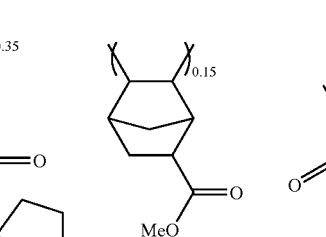
Polymer 11
Mw 8,000
Mw/Mn 1.50
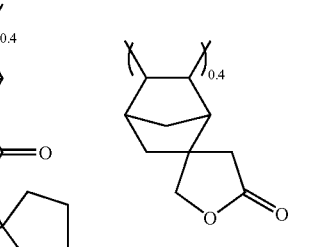
Polymer 12
11,000
Mw/Mn 2.20

-continued

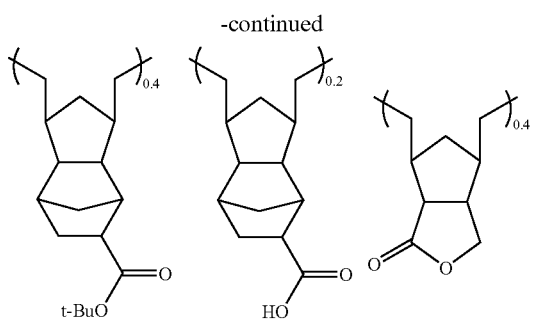

Polymer 13
Mw 12,000
Mw/Mn 2.00

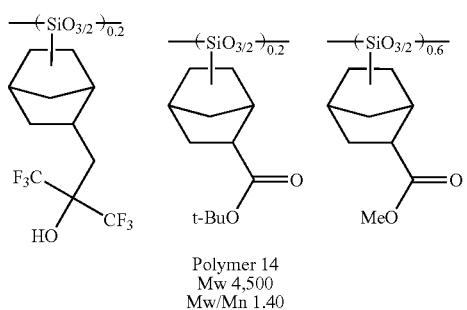

Polymer 14
Mw 4,500
Mw/Mn 1.40

PAG 1

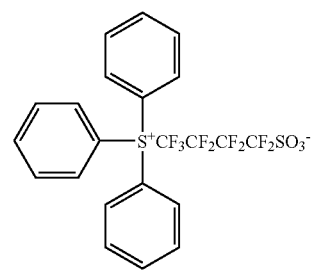

PAG 2

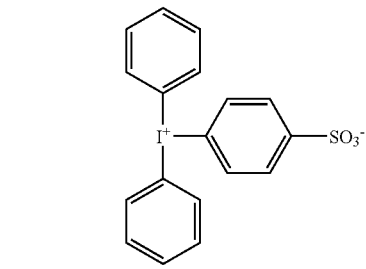

PAG 3

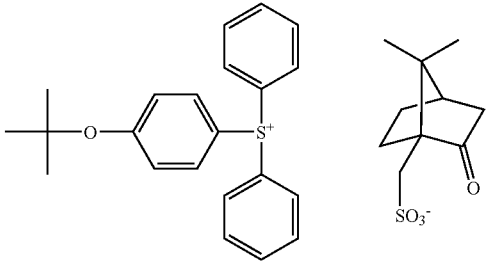

-continued

PAG 4

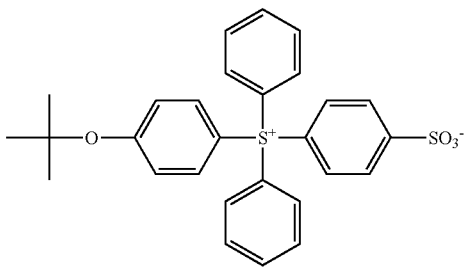

PAG 5

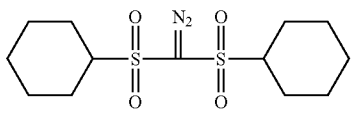

DRI

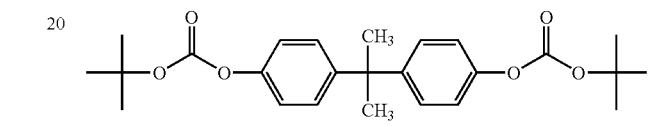

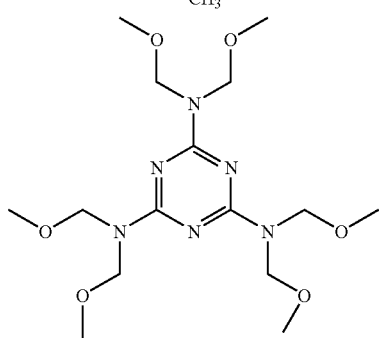

Crosslinker

Example 1

A resist composition was prepared by using the nitrogen-containing organic compound (Amine 1) obtained in Synthesis Example 1, combining it with other components in accordance with the following recipe, and filtering the resulting solution through a Teflon® filter having a pore size of 0.2 µm.

| Components | Parts by weight |
|---|---|
| (A) base polymer (Polymer 3) | 100 |
| (B) photoacid generator (PAG5) | 2.0 |
| (C) Solvent | |
| PGMEA | 280 |
| ethyl lactate | 120 |
| (D) N-containing compound (Amine 1) | 0.1 |

The resulting resist solution was spin-coated onto a silicon wafer substrate having an antireflective coatings (DUV-30 by Nissan Chemical Industries, Ltd., 55 nm) coated thereon, then baked at 120° C. for 90 seconds, forming a resist film of 550 nm thick. The resist film was exposed using an excimer laser stepper NSR-S203B (by Nikon Corporation; NA 0.68, σ 0.75, 2/3 annular illumination), then heat treated at 110° C. for 90 seconds, cooled to 23° C., and subjected to puddle development with a 2.38 wt % aqueous solution of tetramethylammonium hydroxide at 23° C. for 60 seconds, forming a 1:1 line-and-space pattern. The wafer as developed was observed under a top-down SEM. At the optimum exposure dose which provided a 1:1 resolution of a 0.18 μm line-and-space pattern, a 0.15 μm line-and-space pattern was resolved without peeling. A cross section of the resist pattern was also observed to find that the pattern profile was rectangular and perpendicular to the substrate.

Examples 2-24 and Comparative Examples 1-14

Resist compositions were prepared as in Example 1 using the nitrogen-containing organic compounds (Amines 2 to 15) obtained in Synthesis Examples 2 to 15 and comparative nitrogen-containing organic compounds. Note that in Examples and Comparative Examples, amines were used in an equimolar amount to the molar amount calculated from 0.1 pbw of Amine 1. The resist compositions were evaluated for resolution and pattern profile.

Based on the results of these tests, the resolution of the 0.15 μm line-and-space pattern is classified into ratings of passed (○), mediocre (Δ) and rejected (×) as tabulated in Table 1 (Examples) and Table 2 (Comparative Examples), with the pattern profile observed being reported together.

TABLE 1

| Example | Polymer | Photoacid generator | N-containing compound | Dissolution regulator/Crosslinker (pbw) | 0.15 μm resolution | Pattern profile |
|---|---|---|---|---|---|---|
| 1 | Polymer 3 | PAG 5 | Amine 1 | — | ○ | rectangular, perpendicular |
| 2 | Polymer 3 | PAG 5 | Amine 2 | — | ○ | rectangular, perpendicular |
| 3 | Polymer 3 | PAG 5 | Amine 3 | — | ○ | rectangular, perpendicular |
| 4 | Polymer 3 | PAG 5 | Amine 4 | — | ○ | rectangular, perpendicular |
| 5 | Polymer 3 | PAG 5 | Amine 5 | — | ○ | rectangular, perpendicular |
| 6 | Polymer 3 | PAG 5 | Amine 6 | — | ○ | rectangular, perpendicular |
| 7 | Polymer 3 | PAG 5 | Amine 7 | — | ○ | rectangular, perpendicular |
| 8 | Polymer 3 | PAG 5 | Amine 8 | — | ○ | rectangular, perpendicular |
| 9 | Polymer 3 | PAG 5 | Amine 9 | — | ○ | rectangular, perpendicular |
| 10 | Polymer 3 | PAG 5 | Amine 10 | — | ○ | rectangular, perpendicular |
| 11 | Polymer 3 | PAG 5 | Amine 11 | — | ○ | rectangular, perpendicular |
| 12 | Polymer 3 | PAG 5 | Amine 12 | — | ○ | rectangular, perpendicular |
| 13 | Polymer 3 | PAG 5 | Amine 13 | — | ○ | rectangular, perpendicular |
| 14 | Polymer 3 | PAG 5 | Amine 14 | — | ○ | rectangular, perpendicular |
| 15 | Polymer 3 | PAG 5 | Amine 15 | — | ○ | rectangular, perpendicular |
| 16 | Polymer 1 | PAG 5 | Amine 11 | — | ○ | rectangular, perpendicular |
| 17 | Polymer 2 | PAG 5 | Amine 11 | — | ○ | rectangular, perpendicular |
| 18 | Polymer 3 | PAG 4 | Amine 11 | — | ○ | rectangular, perpendicular |
| 19 | Polymer 4 | PAG 2 | Amine 11 | Crosslinker (15) | ○ | rectangular, perpendicular |
| 20 | Polymer 5 | PAG 3 | Amine 11 | — | ○ | rectangular, perpendicular |
| 21 | Polymer 5 | PAG 2 | Amine 11 | DRI (15) | ○ | rectangular, perpendicular |
| 22 | Polymer 6 | PAG 1 | Amine 11 | — | ○ | rectangular, perpendicular |
| 23 | Polymer 7 | PAG 4 | Amine 11 | — | ○ | rectangular, perpendicular |
| 24 | Polymer 8 | PAG 1 | Amine 11 | — | ○ | rectangular, perpendicular |

TABLE 2

| Comparative Example | Polymer | Photoacid generator | N-containing compound/ Dissolution regulator, Crosslinker (pbw) | 0.15 μm resolution | Pattern profile |
|---|---|---|---|---|---|
| 1 | Polymer 3 | PAG 5 | Trioctylamine | X | — |
| 2 | Polymer 3 | PAG 5 | DBU | X | — |
| 3 | Polymer 3 | PAG 5 | TEA | Δ | top-loss, rounded top, tapered |
| 4 | Polymer 3 | PAG 5 | tris(2-methoxyethyl)-amine | X | — |
| 5 | Polymer 3 | PAG 5 | tris(2-acetoxyethyl)-amine | Δ | top-loss, rounded top, tapered |
| 6 | Polymer 1 | PAG 5 | TEA | Δ | top-loss, rounded top, tapered |
| 7 | Polymer 2 | PAG 5 | TEA | X | — |
| 8 | Polymer 3 | PAG 4 | TEA | Δ | top-loss, rounded top, tapered |
| 9 | Polymer 4 | PAG 2 | TEA/Crosslinker (15) | X | — |
| 10 | Polymer 5 | PAG 3 | TEA | Δ | top-loss, rounded top, tapered |
| 11 | Polymer 5 | PAG 2 | TEA/DRI (15) | Δ | top-loss, rounded top, tapered |
| 12 | Polymer 6 | PAG 1 | TEA | X | — |
| 13 | Polymer 7 | PAG 4 | TEA | Δ | top-loss, rounded top, tapered |
| 14 | Polymer 8 | PAG 1 | TEA | X | — |

DBU: 1,8-diazabicyclo[5.4.0]-7-undecene
TEA: triethanolamine

Example 25

A resist composition was prepared by using the nitrogen-containing organic compound (Amine 1) obtained in Synthesis Example 1, combining it with other components in accordance with the following recipe, and filtering the resulting solution through a Teflon® filter having a pore size of 0.2 μm.

| Components | Parts by weight |
|---|---|
| (A) base polymer (Polymer 11) | 80 |
| (B) photoacid generator (PAG1) | 2.0 |
| (C) Solvent (PGMEA) | 640 |
| (D) N-containing compound (Amine 1) | 0.25 |

The resulting resist solution was spin-coated onto a silicon wafer substrate having an antireflective coatings (ARC29A by Nissan Chemical Industries, Ltd., 78 nm) coated thereon, then baked at 130° C. for 60 seconds, forming a resist film of 300 nm thick. The resist film was exposed using an ArF excimer laser stepper (by Nikon Corporation; NA 0.68), then heat treated at 115° C. for 60 seconds, cooled to 23° C., and subjected to puddle development with a 2.38 wt % aqueous solution of tetramethylammonium hydroxide at 23° C. for 60 seconds, forming a 1:1 line-and-space pattern. The wafer as developed was observed under a top-down SEM. At the optimum exposure dose which provided a 1:1 resolution of a 0.15 μm line-and-space pattern, a 0.13 μm line-and-space pattern was resolved without peeling. A cross section of the resist pattern was also observed to find that the pattern profile was rectangular and perpendicular to the substrate.

Examples 26-44 and Comparative Examples 15-24

Resist compositions were prepared as in Example 25 using the nitrogen-containing organic compounds (Amines 2 to 15) obtained in Synthesis Examples 2 to 15 and comparative nitrogen-containing organic compounds. Note that in Examples and Comparative Examples, amines were used in an equimolar amount to the molar amount calculated from 0.25 pbw of Amine 1. The resist compositions were evaluated for resolution and pattern profile.

Based on the results of these tests, the resolution of the 0.13 μm line-and-space pattern is classified into ratings of passed (○), mediocre (Δ) and rejected (×) as tabulated in Table 3 (Examples) and Table 4 (Comparative Examples), with the pattern profile observed being reported together.

TABLE 3

| Example | Polymer | Photoacid generator | N-containing compound | 0.13 μm resolution | Pattern profile |
|---|---|---|---|---|---|
| 25 | Polymer 9 | PAG 1 | Amine 1 | ○ | rectangular, perpendicular |
| 26 | Polymer 9 | PAG 1 | Amine 2 | ○ | rectangular, perpendicular |
| 27 | Polymer 9 | PAG 1 | Amine 3 | ○ | rectangular, perpendicular |
| 28 | Polymer 9 | PAG 1 | Amine 4 | ○ | rectangular, perpendicular |

TABLE 3-continued

| Example | Polymer | Photoacid generator | N-containing compound | 0.13 µm resolution | Pattern profile |
|---|---|---|---|---|---|
| 29 | Polymer 9 | PAG 1 | Amine 5 | ○ | rectangular, perpendicular |
| 30 | Polymer 9 | PAG 1 | Amine 6 | ○ | rectangular, perpendicular |
| 31 | Polymer 9 | PAG 1 | Amine 7 | ○ | rectangular, perpendicular |
| 32 | Polymer 9 | PAG 1 | Amine 8 | ○ | rectangular, perpendicular |
| 33 | Polymer 9 | PAG 1 | Amine 9 | ○ | rectangular, perpendicular |
| 34 | Polymer 9 | PAG 1 | Amine 10 | ○ | rectangular, perpendicular |
| 35 | Polymer 9 | PAG 1 | Amine 11 | ○ | rectangular, perpendicular |
| 36 | Polymer 9 | PAG 1 | Amine 12 | ○ | rectangular, perpendicular |
| 37 | Polymer 9 | PAG 1 | Amine 13 | ○ | rectangular, perpendicular |
| 38 | Polymer 9 | PAG 1 | Amine 14 | ○ | rectangular, perpendicular |
| 39 | Polymer 9 | PAG 1 | Amine 15 | ○ | rectangular, perpendicular |
| 40 | Polymer 10 | PAG 1 | Amine 6 | ○ | rectangular, perpendicular |
| 41 | Polymer 11 | PAG 1 | Amine 6 | ○ | rectangular, perpendicular |
| 42 | Polymer 12 | PAG 1 | Amine 6 | ○ | rectangular, perpendicular |
| 43 | Polymer 13 | PAG 1 | Amine 6 | ○ | rectangular, perpendicular |
| 44 | Polymer 14 | PAG 1 | Amine 6 | ○ | rectangular, perpendicular |

TABLE 4

| Comparative Example | Polymer | Photoacid generator | N-containing compound | 0.13 µm resolution | Pattern profile |
|---|---|---|---|---|---|
| 15 | Polymer 9 | PAG 1 | Trioctylamine | X | — |
| 16 | Polymer 9 | PAG 1 | DBU | X | — |
| 17 | Polymer 9 | PAG 1 | TEA | ○ | top-loss, rounded top, tapered |
| 18 | Polymer 9 | PAG 1 | tris(2-methoxyethyl)-amine | X | — |
| 19 | Polymer 9 | PAG 1 | tris(2-acetoxyethyl)-amine | ○ | top-loss, rounded top, tapered |
| 20 | Polymer 10 | PAG 1 | TEA | ○ | top-loss, rounded top, tapered |
| 21 | Polymer 11 | PAG 1 | TEA | Δ | top-loss, rounded top, tapered |
| 22 | Polymer 12 | PAG 1 | TEA | X | — |
| 23 | Polymer 13 | PAG 1 | TEA | Δ | top-loss, rounded top, tapered |
| 24 | Polymer 14 | PAG 1 | TEA | X | — |

DBU: 1,8-diazabicyclo[5.4.0]-7-undecene
TEA: triethanolamine

It is seen from the above results that the resist compositions within the scope of the invention are improved in resolution and pattern profile.

Japanese Patent Application No. 2004-128478 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A nitrogen-containing organic compound having a 7-oxanorbornane-2-carboxylic ester structure, represented by the general formula (1):

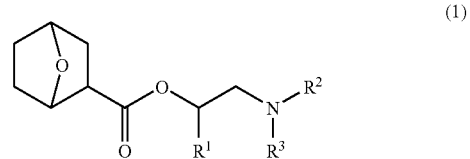

wherein $R^1$ is hydrogen or a straight, branched or cyclic $C_1$-$C_{10}$ alkyl group; $R^2$ and $R^3$ are each independently a $C_1$-$C_{20}$ alkyl group, $C_6$-$C_{20}$ aryl group or $C_7$-$C_{20}$ aralkyl group which may contain at least one polar functional group selected from the group consisting of ether, carbonyl, ester, alcohol, sulfide, nitrile, amine, imine and amide, and wherein the hydrogen atoms of $R^2$ and $R^3$ may be substituted with halogen atoms, or $R^2$ and $R^3$, taken together, may form a heterocyclic or heteroaromatic ring of 2 to 20 carbon atoms with the nitrogen atom to which they are attached.

2. A chemically amplified resist composition comprising at least one nitrogen-containing organic compound of claim 1.

3. A chemically amplified resist composition comprising
(A) the nitrogen-containing organic compound of claim 1,
(B) an organic solvent,
(C) a base resin having an acid labile group-protected acidic functional group which is alkali-insoluble or substantially alkali-insoluble, but becomes alkali-soluble when the acid labile group is eliminated, and
(D) a photoacid generator.

4. A patterning process comprising the steps of:
(1) applying the chemically amplified resist composition of claim 2 onto a substrate;
(2) heat treating the applied resist, then exposing the heat-treated resist through a photomask to high-energy radiation having a wavelength of up to 300 nm or an electron beam; and
(3) heat treating the exposed resist, then developing the resist with a liquid developer. 0

* * * * *